US007615227B2

(12) United States Patent
Klinman et al.

(10) Patent No.: US 7,615,227 B2
(45) Date of Patent: Nov. 10, 2009

(54) USE OF CPG OLIGODEOXYNUCLEOTIDES TO INDUCE ANGIOGENESIS

(75) Inventors: Dennis M. Klinman, Potomac, MD (US); Mei Zheng, Augusta, GA (US); Barry T. Rouse, Knoxville, TN (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 786 days.

(21) Appl. No.: 10/499,597

(22) PCT Filed: Dec. 19, 2002

(86) PCT No.: PCT/US02/40955

§ 371 (c)(1),
(2), (4) Date: Jun. 17, 2004

(87) PCT Pub. No.: WO03/054161

PCT Pub. Date: Jul. 3, 2003

(65) Prior Publication Data

US 2005/0026245 A1    Feb. 3, 2005

Related U.S. Application Data

(60) Provisional application No. 60/343,457, filed on Dec. 20, 2001.

(51) Int. Cl.
*A61K 39/00* (2006.01)
(52) U.S. Cl. .................................................. 424/198.1
(58) Field of Classification Search ....................... None
See application file for complete search history.

(56) References Cited

U.S. PATENT DOCUMENTS

| 2,215,233 A | 9/1940 | Ruskin |
| 3,906,092 A | 9/1975 | Hilleman et al. |
| 3,911,117 A | 10/1975 | Ender |
| 3,914,450 A | 10/1975 | Robbins et al. |
| 4,469,863 A | 9/1984 | Ts'o et al. |
| 4,544,559 A | 10/1985 | Gil et al. |
| 4,741,914 A | 5/1988 | Kimizuka et al. |
| 4,758,553 A | 7/1988 | Ogoshi |
| 4,806,376 A | 2/1989 | Saeki et al. |
| 4,956,296 A | 9/1990 | Fahnestock |
| 4,963,387 A | 10/1990 | Nakagawa et al. |
| 4,994,442 A | 2/1991 | Gil et al. |
| 5,023,243 A | 6/1991 | Tullis |
| 5,066,500 A | 11/1991 | Gil et al. |
| 5,231,085 A | 7/1993 | Alexander et al. |
| 5,234,811 A | 8/1993 | Beutler et al. |
| 5,248,670 A | 9/1993 | Draper et al. |
| 5,268,365 A | 12/1993 | Rudolph et al. |
| 5,288,509 A | 2/1994 | Potman et al. |
| 5,488,039 A | 1/1996 | Masor et al. |
| 5,492,899 A | 2/1996 | Masor et al. |
| 5,585,479 A | 12/1996 | Hoke et al. |
| 5,591,721 A | 1/1997 | Agrawal et al. |
| 5,602,109 A | 2/1997 | Masor et al. |
| 5,612,060 A | 3/1997 | Alexander |
| 5,614,191 A | 3/1997 | Puri et al. |
| 5,650,156 A | 7/1997 | Grinstaff et al. |
| 5,663,153 A | 9/1997 | Hutcerson et al. |
| 5,679,397 A | 10/1997 | Kuroda et al. |
| 5,684,147 A | 11/1997 | Agrawal et al. |
| 5,700,590 A | 12/1997 | Masor et al. |
| 5,712,256 A | 1/1998 | Kulkarni et al. |
| 5,723,335 A | 3/1998 | Hutcerson et al. |
| 5,786,189 A | 7/1998 | Loct et al. |
| 5,804,566 A | 9/1998 | Carson et al. |
| 5,840,705 A | 11/1998 | Tsukuda |
| 5,849,719 A | 12/1998 | Carson et al. |
| 5,895,652 A | 4/1999 | Giampapa |
| 5,919,456 A | 7/1999 | Puri et al. |
| 5,922,766 A | 7/1999 | Acosta et al. |
| 5,976,580 A | 11/1999 | Ivey et al. |

(Continued)

FOREIGN PATENT DOCUMENTS

EP    0 286 224    10/1988

(Continued)

OTHER PUBLICATIONS

Zheng et al. Contribution of vascular endothelial growth factor in the neovascularization process during the pathogenesis of herpetic stromal keratitis. Journal of Virology, Oct. 2001, vol. 75, No. 20, pp. 9828-9835.*
Auf et al. Implication of Macrophages in tumor rejection induced by CpG-oligodeoxynucleotides without antigen. Clinical Cancer Research, Nov. 2001, vol. 7, 3540-3543.*
Hacker et al. CpG-DNA-specific activation of antigen-presenting cells requires stress kinase activity and is preceded by non-specific endocytosis and endosomal maturation. The EMBO Journal, 1998, vol. 17, No. 21, 6230-6240.*
Ghosh et al. Host response to infection: the role of CpG DNA in induction of cyclooxygenase 2 and nitric oxide synthase 2 in murine macrophages. Infection and Immunity, Dec. 2001, vol. 69, No. 12, 7703-7710.*
U.S. Appl. No. 60/156,113.*

(Continued)

*Primary Examiner*—Emily M. Le
(74) *Attorney, Agent, or Firm*—Klarquist Sparkman, LLP

(57) ABSTRACT

This disclosure provides a method of inducing production of vascular endothelial growth factor by a cell. The method includes contacting the cell with a CpG oligonucleotide, thereby inducing the production of vascular endothelial growth factor by the cell. The disclosure further provides a method inducing neovascularization in a tissue. This method includes comprising introducing a CpG oligodeoxynucleotide into an area of the tissue wherein the formation of new blood vessels is desired, thereby inducing neovascularization in the area of the tissue.

19 Claims, 6 Drawing Sheets

U.S. PATENT DOCUMENTS

| | | |
|---|---|---|
| 5,980,958 A | 11/1999 | Naylor et al. |
| 5,994,126 A | 11/1999 | Stienman et al. |
| 6,022,853 A | 2/2000 | Kuberasampath et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,423,539 B2 | 7/2002 | Fong et al. |
| 6,428,788 B1 | 8/2002 | Debinski et al. |
| 6,429,199 B1 | 8/2002 | Krieg et al. |
| 6,498,148 B1 | 12/2002 | Raz |
| 6,514,948 B1 | 2/2003 | Raz et al. |
| 6,534,062 B2 | 3/2003 | Krieg et al. |
| 6,552,006 B2 | 4/2003 | Raz et al. |
| 6,562,798 B1 | 5/2003 | Schwartz |
| 6,589,940 B1 | 7/2003 | Raz et al. |
| 6,610,661 B1 | 8/2003 | Carson et al. |
| 6,613,751 B2 | 9/2003 | Raz et al. |
| 6,653,292 B1 | 11/2003 | Krieg et al. |
| 2001/0034330 A1 | 10/2001 | Kensil |
| 2001/0036462 A1 | 11/2001 | Fong et al. |
| 2001/0044416 A1 | 11/2001 | McCluskie et al. |
| 2001/0046967 A1 | 11/2001 | Van Nest |
| 2002/0006403 A1 | 1/2002 | Yu et al. |
| 2002/0028784 A1 | 3/2002 | Van Nest |
| 2002/0042383 A1 | 4/2002 | Yew et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0065236 A1 | 5/2002 | Yew et al. |
| 2002/0086295 A1 | 7/2002 | Raz et al. |
| 2002/0086839 A1 | 7/2002 | Raz et al. |
| 2002/0090724 A1 | 7/2002 | Taylor et al. |
| 2002/0091095 A1 | 7/2002 | Phillips et al. |
| 2002/0091097 A1 | 7/2002 | Bratzler et al. |
| 2002/0098199 A1 | 7/2002 | Van Nest et al. |
| 2002/0098205 A1 | 7/2002 | Choi et al. |
| 2002/0098980 A1 | 7/2002 | Choi et al. |
| 2002/0107212 A1 | 8/2002 | Van Nest et al. |
| 2002/0110569 A1 | 8/2002 | Granoff et al. |
| 2002/0111323 A1 | 8/2002 | Martin et al. |
| 2002/0136776 A1 | 9/2002 | Fang et al. |
| 2002/0137714 A1 | 9/2002 | Kandimalla et al. |
| 2002/0142974 A1 | 10/2002 | Kohn et al. |
| 2002/0142977 A1 | 10/2002 | Raz et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0183272 A1 | 12/2002 | Johnston et al. |
| 2002/0197269 A1 | 12/2002 | Lingnau et al. |
| 2002/0198165 A1 | 12/2002 | Bratzler et al. |
| 2003/0003579 A1 | 1/2003 | Kadowaki et al. |
| 2003/0022849 A1 | 1/2003 | Chang |
| 2003/0022852 A1 | 1/2003 | Van Nest et al. |
| 2003/0026782 A1 | 2/2003 | Krieg |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0052839 A1 | 3/2003 | Binley et al. |
| 2003/0055014 A1* | 3/2003 | Bratzler .................. 514/44 |
| 2003/0059773 A1 | 3/2003 | Van Nest et al. |
| 2003/0060440 A1 | 3/2003 | Klinman et al. |
| 2003/0064064 A1 | 4/2003 | Dina |
| 2003/0072762 A1 | 4/2003 | Van de Winkel et al. |
| 2003/0073142 A1 | 4/2003 | Chen et al. |
| 2003/0078223 A1 | 4/2003 | Raz et al. |
| 2003/0091599 A1 | 5/2003 | Davis et al. |
| 2003/0092663 A1 | 5/2003 | Raz |
| 2003/0096417 A1 | 5/2003 | Fischer |
| 2003/0100527 A1 | 5/2003 | Krieg et al. |
| 2003/0104044 A1 | 6/2003 | Semple et al. |
| 2003/0104523 A1 | 6/2003 | Lipford et al. |
| 2003/0109469 A1 | 6/2003 | Carson et al. |
| 2003/0119773 A1 | 6/2003 | Raz et al. |
| 2003/0119774 A1 | 6/2003 | Foldvari et al. |
| 2003/0119776 A1 | 6/2003 | Phillips et al. |
| 2003/0125284 A1 | 7/2003 | Raz et al. |
| 2003/0129251 A1 | 7/2003 | Van Nest et al. |
| 2003/0130217 A1 | 7/2003 | Raz et al. |
| 2003/0133988 A1 | 7/2003 | Fearon et al. |
| 2003/0135875 A1 | 7/2003 | Ehrhardt et al. |
| 2003/0138413 A1 | 7/2003 | Vicari et al. |
| 2003/0138453 A1 | 7/2003 | O'Hagan et al. |
| 2003/0139364 A1 | 7/2003 | Krieg et al. |
| 2003/0143213 A1 | 7/2003 | Raz et al. |
| 2003/0143743 A1 | 7/2003 | Schuler et al. |
| 2003/0144229 A1 | 7/2003 | Klinman et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0148983 A1 | 8/2003 | Fontoura et al. |
| 2003/0157717 A1 | 8/2003 | Draghia-Akli |
| 2003/0158136 A1 | 8/2003 | Rice et al. |
| 2003/0165478 A1 | 9/2003 | Sokoll |
| 2003/0166001 A1 | 9/2003 | Lipford |
| 2003/0170273 A1 | 9/2003 | O'Hagan et al. |
| 2003/0171321 A1 | 9/2003 | Schmidt et al. |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0180320 A1 | 9/2003 | Darju et al. |
| 2003/0181406 A1 | 9/2003 | Schetter et al. |
| 2003/0185848 A1 | 10/2003 | Johnston et al. |
| 2003/0185900 A1 | 10/2003 | Choi et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0203861 A1 | 10/2003 | Carson et al. |
| 2003/0206967 A1 | 11/2003 | Choi et al. |
| 2003/0207287 A1 | 11/2003 | Short |
| 2003/0212026 A1* | 11/2003 | Krieg et al. .................. 514/44 |
| 2003/0212028 A1 | 11/2003 | Raz et al. |
| 2003/0216340 A1 | 11/2003 | Van Nest et al. |
| 2003/0219752 A1 | 11/2003 | Short |
| 2003/0220277 A1 | 11/2003 | Yew et al. |
| 2003/0224010 A1 | 12/2003 | Davis et al. |
| 2003/0225016 A1 | 12/2003 | Fearon et al. |
| 2003/0232780 A1 | 12/2003 | Carson et al. |
| 2004/0005588 A1 | 1/2004 | Cohen et al. |
| 2004/0006010 A1 | 1/2004 | Carson et al. |
| 2004/0006032 A1 | 1/2004 | Lopez |
| 2004/0006034 A1 | 1/2004 | Raz et al. |
| 2004/0009897 A1 | 1/2004 | Sokoll |
| 2004/0009942 A1 | 1/2004 | Van Nest |
| 2004/0009949 A1 | 1/2004 | Krieg |
| 2004/0013686 A1 | 1/2004 | Granoff et al. |
| 2004/0013688 A1 | 1/2004 | Wise et al. |
| 2004/0028693 A1 | 2/2004 | Wu et al. |

FOREIGN PATENT DOCUMENTS

| | | |
|---|---|---|
| EP | 0 302 758 | 11/1989 |
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |

| | | |
|---|---|---|
| WO | WO 92/03456 | 4/1992 |
| WO | WO 92/18522 | 10/1992 |
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |
| WO | WO 97/28259 | 1/1997 |
| WO | WO 98/29430 | 12/1997 |
| WO | WO 98/11211 | 3/1998 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/40100 | 9/1998 |
| WO | WO 98/49288 | 11/1998 |
| WO | WO 98/49348 | 11/1998 |
| WO | WO 98/52581 | 11/1998 |
| WO | WO 98/55495 | 12/1998 |
| WO | WO 99/11275 | 3/1999 |
| WO | WO 99/37151 | 7/1999 |
| WO | WO 99/51259 | 10/1999 |
| WO | WO 99/56755 | 11/1999 |
| WO | WO 99/58118 | 11/1999 |
| WO | WO 99/61056 | 12/1999 |
| WO | WO 99/62923 | 12/1999 |
| WO | WO 00/14217 | 3/2000 |
| WO | WO 00/20039 | 4/2000 |
| WO | WO 00/21556 | 4/2000 |
| WO | WO 00/06588 | 10/2000 |
| WO | WO 00/61151 | 10/2000 |
| WO | WO 00/62787 | 10/2000 |
| WO | WO 00/67023 | 11/2000 |
| WO | WO 00/67787 | 11/2000 |
| WO | WO 01/00232 | 1/2001 |
| WO | WO 01/02007 | 1/2001 |
| WO | WO 01/12223 | 2/2001 |
| WO | WO 01/12804 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 02/69369 | 9/2002 |

OTHER PUBLICATIONS

Honess et al. Deviations from Expected Frequencies of CpG Dinucleotides in Herpes Virus DNA May be Diagnostic of Differences in The States of Their Latent Genomes, *J. Gen Vir.* 70(4):837-855, 1989

Ishibashi et al., SPI Decoy Transfected to Carcinoma Cells Suppresses The Expression of Vascular Endothelial Growth Factor, Transfomring Growth Factor B-1, and Tissue Factor and Also Cell Growth and Invasion Activities, *Cancer Research* 60:6531-6536, 2000.

Zheng et al., Contribution of Vascular Endothelial Growth Factor in The Neovasularization Process During The Pathogenesis of Herpetic Stromal Keratitis. *J. Virol.* 75(20):9828-9835, 2001.

US 6,008,200, 12/1999, Krieg (withdrawn).

Adya, et al., "Expansion of CREB's DNA recognition specificity by Tax results from interaction with Ala-Ala-Arg at positions 282-284 near the conserved DNA-binding domain of CREB". Proc. Natl. Acad. Sci. USA 91(12):5642-5646 (1994).

Agrawal, et al., "Pharmacokinetics of Oligonucleotides". Ciba. Found. Symp. 209:60-78 (1997), abstract.

Agrawal, et al., "Pharmacokinetics and Bioavailability of Antisense Oligonucleotides Following Oral and Colorectal Adminstration of Experimental Animals". Handb. Exp. Pharmacol.: Antisense Research and Application 131:525-543 (1998).

Agrawal, "Antisense Oligonucleotides: Toward Clinical Trials". Tibtech 14:376-387 (1996).

Agrawal, et al., "In Vivo Pharmacokinetics of Phosphorothioate Oligonucleotides Containing Contiguous Guanosines". Antisense & Nucleic Acid Drug Development 7:245-249 (1997).

Agrawal, et al., "Absorption, Tissue Distribution and In Vivo Stability in Rats of a Hybrid Antisense Oligonucleotide Following Oral Administration". Biochemical Pharmacology 50(4):571-576 (1995).

Agrawal, et al., "Pharmacokinetics of Antisense Oligonucleotides". Clin. Pharmacokinet 28(1):7 (1995).

Agrawal, et al., "Antisense therapeutics: is it as simple as complementary base recognition?". Molecular Med. Today 6(2):72-81 (2000), abstract.

Agrawal, et al., "Pharmacokinetics, biodistribution, and stability of oligodeoxynucleotide phosphorothioates in mice". Proc. Natl. Acad. Sci. USA 88:7595-7599 (1991).

Agrawal, "Medicinal Chemistry and Therapeutic Potential of CpG DNA". Trends in Molecular Medicine 8(3):114-121 (2002).

Alama, et al., "Antisense Oligonucleotides as Therapeutic Agents". Pharmacol. Res. 36:171-178 (1997).

Amaral, et al., "Leishmania amazonensis: The asian rhesus macaques (*Macaca mulatta*) as an experimental model for study of cutaneous leishmaniasis". Exp. Parasitol. 82(1):34-44 (1996).

Anderson, "Human Gene Therapy". Nature 392:25-30 (Apr. 1998).

Anderson, et al., "TH2 and 'TH2-like' cells in allergy and asthma; pharmacological perspectives". TiPS 15:324-332 (1994).

Anfossi, et al., "An oligomer complementary to c-myb-encoded mRNA inhibits proliferation of human myeloid leukemia cell lines". Proc. Natl. Acad. Sci. USA 86:3379-3383 (May 1989).

Angier, "Microbe DNA seen as alien by immune system". New York Times p. C1, 2 pages (1995).

Azad, et al., "Antiviral activity of a phosphorothioate oligonucleotide complementary to RNA of the human cytomegalovirus major immediate-early region". Amtimicrobial Agents and Chemotherapy 37:1945-1954 (1993).

Azuma, "Biochemical and immunological studies on cellular components of tubercle bacilli". Kekkaku 69(9):45-55 (1992).

Azzoni, et al., "Sustained Impairment of IFN-γ Secretion in Suppressed HIV-Infected Patients Despite Mature NK Cell Recovery: Evidence for a Defective Reconstruction of Innate Immunity". J. Immunol. 168(11):5764-5770 (2002).

Ballas, et al., "Induction of NK activity in murine and human cells by CpG motifs in oligodeoxynucleotides and bacterial DNA". J. Immunol. 157(5):1840-1845 (1996).

Banchereau, et al., "Immunobiology of Dendritic Cells". Ann. Rev. Immunol. 18:767-811 (2000).

Banchereau & Steinman, "Dendritic Cells and the Control of Immunity". Nature 392:245-252 (1998).

Barouch, et al., "Control of Viremia and Prevention of Clinical AIDS in Rhesus Monkeys by Cytokine-Augmented DNA Vaccination". Science 290:486-492 (Oct. 2000).

Bauer, et al., "Bacterial CpG-DNA Triggers Activation and Maturation of Human CD11c-, CD123+ Dendritic Cells". J. Immunol. 166:5000-5007 (2001).

Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383-390 (1993).

Benimetskaya, et al., "Formation of a G-tetrad and higher order structures correlates with biological activity of the RelA (NF-kBp65) 'antisense' oligodeoxynucleotide". Nucleic Acids Research 25(13):2648-2656 (1997).

Bennett, et al., "DNA binding to human leukocytes: evidence for a recptor-mediated association, internalization, and degradation of DNA". J. Clin. Invest. 76(6):2182-2190 (1985).

Berg, et al., "Interleukin-10 is a central regulator fo the response to LPS in murine models of endotoxic shock and the Shwartzman reaction but not endotoxin tolerance". J. Clin. Invest. 96(5):2339-2347 (1995).

Biolabs, "1988-1989 Catalog, Random Primer #s 1230, 1601, 1602". ().

Bishop, et al., "Intramolecular G-quartet Motifs Confer Nuclease Resistance to a Potent Anti-HIV Oligonucleotide". The Journal of Biological Chemistry 271(10):5698-5703 (Mar. 1996).

Blanchard, et al., "Interferon-y Induction by Lipopolysaccharide: Dependence of Interleukin 2 and Macrophages". The Journal of Immunology 136(3):963-970 (Feb. 1986).

Blanco, et al., "Induction of Dendritic Cell Differentiation by IFN-α in Systemic Lupus Erythermatosus". Science 294:1540-1543 (2001).

Blaxter, et al., "Genes expressed in *Brugia malayi* infective third stage larvae". Mol. Biochem. Parasitol. 77:77-93 (1996).

Boggs, et al., "Characterization and modulation of immune stimulation by modified oligonucleotides". Antisense Nucl. Acid Drug Dev. 7(5):461-471 (1997).

Boiarkina, et al., "Dietary supplementals from ground fish meat with DNA for treatment and prophylaxis". Vopr. Pitan 1:29-31 (1998), abstract.

Branda, et al., "Immune stimulation by an antisense oligomer complementary to the rev gene of HIV-1". Biochem. Pharmacol. 45(10):2037-2043 (1993).

Branda, et al., "Amplification of antibody production by phosphorothioate oligodeoxynucleotides". J. Lab Clin. Med. 128(3):329-338 (1996).

Briskin, et al., "Lipopolysaccharide-unresponsive mutant pre-B-cell lines blocked in NF-kappa B activation". Mol. Cell Bio. 10(1):422-425 (1990).

Burgess, "The antiproliferative activity of c-myb and c-myc antisense oligonucleotides in smooth muscle cells is caused by a nonantisense mechanism". Proc. Natl. Acad. Sci. USA 92:4051-4055 (Apr. 1995).

Calarota, et al., "Immune Responses in Asymptomatic HIV-1 Infected Patients After HIV-DNA Immunization Followed by Highly Active Antiretroviral Threatment". J. Immunol. 163(4):2330-2338 (1999).

Chace, et al., "Regulation of differentiation in CD5+ and conventional B cells". Clin. Immunol. Immunopathol. 68(3):327-332 (1993).

Chang, et al., "The palindromic series I repeats in the simian cytomegalovirus major immediate-early promoter behave as both strong basal enhancers and cyclic AMP response elements". J. Virol. 64(1):264-277 (1990).

Chapuis, et al., "Differentiation of Human Dendritic Cells from Monocytes in vitro". Eur. J. lmmunol. 27:431-441 (1997).

Chehimi, "Persistent Decreases in Blood Plasmacytoid Dendritic Cell Number and Function Despite Effective Highly Active Antiretroviral Therapy and Increased Blood Myeloid Dendritic Cells in HIV-Infected Individuals". J. lmmunol. 168(9):4796-4801 (2002).

Chu, et al., "CpG oligodeoxynucleotides act as adjuvants that switch on T helper 1 (Th1) immunity". J. Exp. Med. 186(10):1623-1631 (1997).

Chun, et al., "Effect of interleukin-2 on the pool of latently infected, resting CD4+ T-cells in HIV-1-infected patients receiving highly active anti-retroviral therapy". Nature Med. 5(6):651-655 (1999).

Chun, et al., "Perspective: Latent reservoirs of HIV: Obstacles to the eradication of virus". Proc. Natl. Acad. Sci. USA 96:10958-10961 (1999).

Cohen, et al., "Exploring How to Get at—and Eradicate—Hidden HIV". Science 279:1854-1855 (1998).

Cohen & Fauci, et al., "HIV/AIDS in 1998—Gaining the Upper Hand?". JAMA 280(1):87-88 (1998).

Cook, et al., "Effect of a Single Ethanol Exposure on HIV Replication in Human Lymphocytes". J. Invest. Med. 45(5):265-271 (1997).

Cooper, et al., "Therapeutic Strategies for HIV Infection—Time To Think Hard". The New England Journal of Medicine 339(18):1319-1321 (1998).

Cowdery, et al., "Bacterial DNA induces NKcells to produce IFN-gamma in vivo and increases the toxici of lipopolysaccharides". J. Immunol. 156(12):4570-4575 (1996).

Crosby, et al., "The early responses gene NGFI-C encodes a zinc finger transcriptional activator and is a member of the GCGGGGGCG (GSG) element-binding protein family". Mol. Cell Bio. 2:3835-3841 (1991).

Crystal, "Transfer of genes to humans: early lessons and obstacles to success". Science 270:404-410 (1995).

Cryz, et al., "Vaccine Delivery System—European Commission COST/STD Initiative Report of the Expert Panel VII". Vaccine 14(7):665-690 (1996).

D'Andrea, et al., "Interleukin 10 (IL-10) inhibits human lymphocyte interferon gamma-production by suppressing natural killer cell stimulatory factor/IL-12 synthesis in accessory cells". J. Exp. Med. 178(3):1041-1048 (1993).

Davey, et al., "HIV-1 and T-Cell dynamics after interruption of highly antiretroviral therapy (HAART) in patients with a history of sustained viral suppression". Proc. Natl. Acad. Sci. USA 96(26):15109-15114 (1999).

Davis, et al., "CpG DNA is a Potent Enhancer of Specific Immunity in Mice Immunized with Recombinant Hepatitis B Surface Antigen". J. Immunol. 160(2):870-876 (1998).

Davis, "Plasmid DNA expression systems for the purpose of immunization". Curr. Opin. Biotechnol. 8(5):635-646 (Oct. 1997).

Dematos, et al., "Pulsing of Dendritic Cells with Cell Lysates from Either B16 Melanoma or MCA-106 Fibrosarcoma Yields Equally Effective Vaccines Against B16 Tumors in Mice". J. Surg. Oncol. 68:79-91 (1998).

Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).

Dias et al., "Antisense Oligonucleotides: Basic Concepts and Mechanisms," *Mol. Cancer Ther.* 1:317-355, 2002.

Doerfler, et al., "On the Insertion of Foreign DNA into Mammalian Genomes: Mechanism and Consequences". Gene 157(1-2):241-254 (1995), abstract.

Durham, et al., "Immunotherapy and Allergic Inflammation". Clin. Exp. Allergy 21 Suppl 1:206-210 (1991).

Eck, et al., "Chapter 5: Gene-Based Therapy". Goodman & Gilman's The Pharmacological Basis of Therapeutics 9th ed.:77-101 (1996).

Elkins, et al., "Bacterial DNA containing CpG motifs stimulates lymphocyte-dependent protection of mice against lethal infection with intracellular bacteria". J. Immunol. 162:2291-2298 (1999).

Englisch, et al., "Chemically modified oligonucleotides as probes and inhibitors". Angew. Chem. Int. Ed. Engl. 30:613-629 (1991).

Erb, et al., "Infection of mice with Mycobacterium bovis-badillus Calmette-Guerin (BCG) supresses allergen-induced airway eosinophilia". J. Exp. Med. 184(4):561-569 (1998).

Etlinger, "Carrier sequence selection—one key to successful vaccines". Immunology Today 13(2):52-55 (1992).

Fanslow, et al., "Effect of Nucleotide Restriction and Supplementation on Resistance to Experimental Murine Candidasis". J. Parenter. Enteral. Nutr. 12(1):49-52 Abstract (1988).

Fields, et al., "Murine Dendritic Cells Pulsed With Whole Tumor Lysates Mediate Potent Antitumor Immune Responses in vitro and in vivo". Proc. Natl. Acad. Sci. USA 95:9482-9487 (1998).

Filion, et al., "Major Limitations in the use of Cationic Liposomes for DNA Delivery". Int. J. Pharmaceuticals 162:159-170 (1998).

Fox, "Mechanism of action of hydroxychloroquine as an antirheumatic drug". Chem. Abstracts 120:15, Abstract No. 182630 (1 page) (1994).

Freidag, et al., "CpG oligodeoxynucleotides and interleukin-12 improve the efficacy of Mycobacterium bovis BCG vaccination in mice challenged with M. tuberculosis". Infect. Immun. 68:2948-2953 (2000).

Gao, et al., "Phosphorothioate oligonucleotides are inhibitors of human DNA polymerases and Rnase H: Implications for antisense technology". Mol. Pharmacol. 41:223-229 (1992).

Garraud, "Regulation of Immunoglobin Production in Hyper-IgE (Job's) Syndrome". J. Allergy Clin. lmmunol. 103(2 Pt 1):333-340 (Feb. 1999).

Gluckman, et al., "In Vitro Generation of Human Dendritic Cells and Cell Therapy". Cytokines Cell Mol. Ther. 3:187-196 (1997).

Gramzinski, et al., "Interleukin-12- and gamma interferon-dependent protection against malaria conferred by CpG oligodeoxynucleotide in mice". Infect. lmmun. 69(3):1643-1649 (2001).

Gura, "Antisense has growing pains". Science 270:575-576 (1995).

Gursel, "Sterically Stabilized Cationic Liposomes Improve the Uptake and Immunostimulatory Activity of CpG Oligonucleotides". J. Immunol. 167(6):3324-3328 (2001).

Gursel, et al., "Differential and Competitive Activation of Human Immune Cells by Distinct Classes of CpG Oligodeoxynucleotide". J. Leuko. Biol. 71:813-820 (2002).

Hadden, et al., "Immunopharmacology". JAMA 268(20):2964-2969 (1992).

Hadden, et al., "Immunostimulants". TiPS 141:169-174 (1993).

Halpern, et al, "Bacterial DNA induces murine interferon-gamma production by stimulation of interleukin-12 and tumor necrosis factor-alpha". Cell Immunol. 167(1):72-78 (1996).

Haslett, et al., "Strong Human Immunodificiency Virus (HIV) Specific CD4+ T Cell Responses in a Cohort of Chronically Infected Patients are Associated with Interruptions in Anti-HIV Chemotherapy". J. Infect. Diseases 181:1264-1272 (2000).

Hatzfeld, "Release of early human hematopoietic progenitors from quiescence by antisense transformin owth factor β1 or Rb oligonucleotides". J. Exp. Med. 174:925-929 (1991).

Havlir, et al., "Maintenance Antiretroviral Therapies in HIV-Infected Subjects with Undetectable Plasma HIV RNA after Triple-Drug Therapy". The New England Journal of Medicine 339(18):1261-1268 (1998).

Hayashi, et al., "Enhancement of innate immunity against Mycobacterium avium infection by immunostimutatory DNA is mediated by indoteamine 2,3-dioxygenase". Infect. Immun. 69:6156-6164 (2001).

Hertl, et al., "Inhibition of Interferon-y-Induced Intercellular Adhesion Molecule-1 Expression on Human Keratinocytes by Phosphorothioate Antisense Oligodeoxynucleotides is the Consequence of Antisense-Specific and Antisense-Non-Specific Effects". The Journal of Investigative Dermatology 104(5):813-818 (May 1995).

Highfield, "Sepsis: the more, the murkier". Biotechnology 12:828 (1994).

Honess, et al., "Deviations from Expected Frequencies of CpG Dinucleotides in Herpesvirus DNAs May be Diagnostic of Differences in the States of Their Latent Genomes". J. Gen. Vir. 70(4):837-855 (1989).

Hoeffler, et al., "Identification of multiple nuclear factors that interact with cyclic adenosine 3',5'-monophosphate response element-binding protein and activating transcription factor-2 by protein-protein interactions". Mol. Endocrinol. 5(2):256-266 (1991).

Horspool, et al., "Nucleic acid vaccine-induces immune responses require CD28 costimulation and are regulated by CTLA4". J. Immunol. 160:2706-2714 (1998).

Hughes, et al., "Influence of Base Composition on Membrane Binding and Cellular Uptake of 10-mer Phosphorothioate Oligonucleotides in Chinese Hamster Ovary (CHRC5) Cells". Antisense Research and Development 4:211-215 (1994).

Iguchi-Ariga, et al., "CpG methylation of the cAMP-responsive enhancer/promoter sequence TGACGTCA abolishes specific factor binding as well as transcriptional activation". Genes Dev. 3(5):612-619 (1989).

Imami, et al., "Assessment of Type 1 and Type 2 Cytokines in HIV Type 1-Infected Individuals: Impact of Highly Active Antiretroviral Therapy". AIDS Research and Human Retroviruses 15(17):1499-1508 (1999).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Ishikawa, et al., "IFN induction and associated changes in splenic leukocyte distribution". J. Immunol. 150(9):3713-3727 (1993).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jakway, et al., "Growth regulation of the B lymphoma cell line WEHI-23 1 by anti-immunoglobulin, lipopolysaccharide, and other bacterial products". J. Immunol. 137(7):2225-2231 (1996).

Jaroszewski, et al., "Cellular uptake of antisense oligonucleotides". Adv. Drug Delivery Rev. 6(3):235-250 (1991).

Jilek, et al., "Antigen-Independent Suppression of the Allergic Immune Response to Bee Venom Phospholipase A2 by DNA Vaccination in CBA/J Mice". J. Immunol. 166:3612-3621 (2001).

Jones, et al., "Synthetic Oligonucleotides Containing CpG Motifs Enhance Immunogenicity of a Peptide Malaria Vaccine in Aotus Monkeys". Vaccine 17:3065-3071 (1999).

Juffermans, et al., "CpG oligodeoxynucleotides enhance host defense during murine tuberculosis". Infect. Immun. 70:147-152 (2002).

Kadowaki, et al., "Distinct CpG DNA and Polyinosinic-Polycytidylic Acid Double Stranded RNA, Respectively, Stimulate CD11c- Type 2 Dendritic Cell Precursoes and CD11c+ Dendritic cells to Produce Type I IFN". J. Immunol. 166:2291-2295 (2001).

Kataoka, et al., "Antitumor activity of synthetic oligonucleotides with sequences from cDNA encodin proteins of Mycobacterium bovis BCG". Jpn. J. Cancer Res. 83:244-247 (1992).

Kenney, et al., "Protective Immunity Using Recombinant Human IL-12 and Alum as Adjuvants in a Primate Model of Cutaneous Leishmaniasis". J. Immunol. 163(8):4481-4488 (1999).

Khaled, et al., "Multiple mechanisms may contribute to the cellular anti-adhesive effects of phosphorothioate oligodeoxynucleotides". Nucleic Acids Research 24(4):737-745 (1996).

Kimura, et al., "Binding of oligoguanylate to scavenger receptors is required for oligonucleotides to augment NK cell activity and induce IFN". J. Biochem 116(5):991-994 (1994).

Kline, et al., "CpG motif oligonucleotides are effective in prevention of eosinophilic inflammation in a murine model of asthma". J. Invest. Med. 44(7):380A (1 page) (1996).

Kline, et al., "CpG oligonucleotides can reverse as well as prevent TH2-mediated inflammation in a murine model of asthma". J. Invest. Med. 45(7):298A (1 page) (1997).

Kline, et al., "Immune redirection by CpG oligonucleotides, Conversion of a Th2 response to a Th1 response in a murine model of asthma". J. Invest. Med. 45(3):282A (1 page) (1997).

Klinman, et al., "Immune recognition of foreign DNA: a cure for bioterrorism?". Immunity 11:123 (1 page) (1999).

Klinman, et al., "Repeated administration of synthetic oligodeoxynucteotides expressing CpG motifs provides tong-term protection against bacterial infection". Infect. Immun. 67:5658-5663 (1999).

Klinman, et al., "CpG motifs present in bacteria DNA rapidly induce lymphocytes to secrete interleukin 6, interleukin 12, and interferon gamma". Proc. Natl. Acad. Sci. USA 93(7):2879-2883 (1996).

Klinman, et al., "Activation of the innate immune system by CpG oligodeoxynucleotides: immunoprotective activity and safety". Springer Semin. Immunopathol. 22:173-183 (2000).

Klinman, et al., "CpG Motids as Immune Adjuvants". Vaccine 17:19-25 (1999).

Kou, et al., "Analysis and Regulation of interferon-gamma production by peripheral blood lymphocytes from patients with bronchial asthma". Arerugi 43(3):483-491 (1994), abstract.

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Phosphorothioate oligodeoxynucleotides: antisense or anti-protein?". Antisense Res. Dev. 5:241 (1 page) (1995).

Krieg, et al., "Uptake of oligodeoxyribonucleotides by lymphoid cells is heterogeneous and inducible". Antisense Res. Dev. 1(2):161-171 (1991).

Krieg, et al., "Leukocyte stimulation by oligodeoxynucleotides". Applied Antisense Oligonucleotide Tech. (Book):431-448 (1998).

Krieg, et al., "Causing a Commotion in the Blood: Immunotherapy Progresses from Bacteria to Bacterial DNA". Immunology Today 21(10):521-526 (2000).

Krieg, et al., "CpG DNA: A pathogenic factor in systemic lupus erythematosus?". J. Clin. Immunol. 15(6):284-292 (1995).

Krieg, et al., "CpG DNA induces sustained IL-12 expression in vivo and resistance to Listeria monocytogenes challenge". J. Immunol. 161:2428-2434 (1998).

Krieg, et al., "A role for endogenous retroviral sequences in the regulation of lymphocyte activation". J. Immunol. 143(8):2448-2451 (1989).

Krieg, "An innate immune defense mechanism based on the recognition of CpG motifs in microbial DNA". J. Lab. Clin. Med. 128(2):128-133 (Abstract) (1996).

Krieg, et al., "CpG motifs in bacterial DNA trigger direct B-cell activation". Nature 374:546-549 (1995).

Krieg, et al., "Modification of antisense phosphodiester oligodeoxynucleotides by a 5' cholesteryl moiety increases cellular association and improves efficacy". Proc. Natl. Acad. Sci. USA 90:1048-1052 (1993).

Krieg, et al., "The role of CpG dinucleotides in DNA vaccines". Trends in Microbiol. 6:23-27 (1998).

Krieger, et al., "Structures and Functions of Multiligand Lipoprotein Receptors: Macrophage Scavenger Receptors and LDL Receptor-Related Protein (LRP)". Annu. Rev. Biochem 63:601-637 (1994).

Krug, et al., "Identification of CpG Oligonucleotide Sequences with High Induction of IFN-α/β in Plasmacytoid Dendritic Cells". Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12". Eur. J. Immunol. 31:3026-3037 (2001).

Kuchan, et al., "Nucleotides in Infant Nutrition: Effects of Immune Function". Pediatr. Adolesc. Med. Basel. Karger 8:80-94 (1998).

Kulkarni, et al., "Effect of Dietary Nucleotides on Response to Bacterial Infection". J. Parenter. Enteral. Nutr. 10(2):169-171 Abstract (1986).

Kuramoto, et al., "Oligonucleotide sequences required for natural killer cell activation". Jpn. J. Cancer Res. 83:1128-1131 (1992).

Lagrange, et al., "Immune Responses Directed Against Infectious and Parasitic Agents". Immunology (Book—ISBN:0471017604) (Chapter of Book; Ed—Jean-François Bach): (1978).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357-370 (Oct. 1998).

Ledergerber, et al., "Clinical Progression and Virological Failure on Highly Active Antiretroviral Therapy in HIV-1 Patients: a Prospective Cohort Study". The Lancet 353:863-868 (1999).

Lederman, et al., "Polydeoxyguanine Motifs in a 12-mer Phosphorothioate Oligodeoxynucleotide Augment Binding to the v3 Loop of the HIV-1 gp120 and Potency of HIV-1 Inhibition Independently of G-Tetrad Formation". Antisense & Nucleic Acid Drug Development 6:281-289 (1996).

Lee, et al., "An Oligonucleotide Blocks Interferon-γ Signal Transduction". Transplantation 62(9)1297-1301 (1996).

Leibson, et al., "Role of γ-interferon in antibody-producing responses". Nature 309:799-801 (1984).

Leonard, et al., "Conformation of guanine 8-oxoadenine base pairs in the crystal structure of d(CGCGAATT(O8A)GCG)". Biochemistry 31(36):8415-8420 (1992).

Li, et al., "Long-Lasting Recovery in CDR T-Cell Function and Viral -Load Reduction After Highly Active Antiretroviral Therapy in Advanced HIV-1 Disease". The Lancet 351:1682-1686 (1998).

Liang, et al., "Activation of Human B Cells by Phosphorothioate Oligodeoxynucleotides". J. Clin. Invest. 98:1119-1129 (1996).

Lipford, et al., "CpG-containing synthetic oligonucleotides promote B and cytotoxic T cell responses to protein antigen: a new class of vaccine adjuvants". Eur. J. Immunol. 27(9):2340-2344 (1997).

Lipford, et al., "Immunostimulatory DNA: sequence-dependent production of potentially harmful or useful cytokines". Eur. J. Immunol. 27(12):3420-3426 (1997).

Lönnberg, et al., "Towards Genomic Drug Therapy with Antisense Oligonucleotides". Ann. Med. 28:511-522 (1996).

Macaya, et al., "Thrombin-binding DNA aptamer forms a unimolecular quadruplex structure in solution". Proc. Natl. Acad. Sci. USA 90:3745-3749 (Apr. 1993).

Macfarlane, et al., "Antagonism of immunostimulatory CpG-oligodeoxynucleotides by quinacrine, chloroquine, and structurally related compounds". J. Immunol. 160(3):1122-1131 (1998).

Maddon, "The Isolation and Nucleotide Sequence of a cDNA Encoding the T Cell Surface Protein T4: A New Member of the Immunoglobin Gene Family". Cell 42(1):93-104 (1985).

Maltese, et al., "Sequence context of antisense RelA/NF-kB phohphorothioates determines specificity". Nucleic Acids Research 23(7):1146-1151 (1995).

Manzel, et al., "Lack of Immune Stimulation by Immobilized CpG-oligonucletide". Antisense & Nucleic Acid Drug Development 9(5):459-464 (1999).

Mastrangelo, et al., "Gene therapy for human cancer: an essay for clinicians". Seminars Oncology 23(1):4-21 (1996).

Matson, et al., "Nonspecific suppression of [3H]thymidine incorporation by control oligonucleotides". Antisense Res. Dev. 2(4):325-330 (1992).

McCluskie, et al., "Cutting Edge: CpG DNA Is a Potent Enhancer of Systemic and Mucosal Immune Responses Against Hepatitis B Surface Antigen with Intranasal Administration to Mice". J. Immun. 161:4463-4465 (1998).

McCluskie, et al., "Route and Method of DNA Vaccine Influence Immune Responses in Mice and Non-Human Primates". Molecular Med. 5(5):287-300 (1999).

McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).

McKenzie, "Nucleic Acid Vaccines". Immunologic Res. 24(3):225-244 (2001).

Merad, et al., "In vivo Manipulation of Dendritic Cells to Induce Therapeutic Immunity". Blood 99(5):1676-1682 (2002).

Messina, et al., "Stimulation of in vitro murine lymphocyte proliferation by bacterial DNA". Cell Immunol. 147(6):1759-1764 (1991).

Messina, et al., "The influence of DNA structure on the in vitro stimulation of murine lymphocytes by natural and synthetic polynucleotide antigens". J. Immunol. 147:148-157 (1993).

Mojcik, et al., "Administration of a phosphorothioate oligonucleotide antisense murine endogenous retroviral MCF env causes immune effect in vivo in a sequence-specific manner". Clin. Immunol. Immunopathol. 67(2):130-136 (1993).

Moss & Lederman, "Immunication of the Immunocompromised Host". Clinical Focus on Primary Immune Deficiencies 1(1):1-3 (1998).

Mottram, et al., "A novel CDC2-related protein kinase from leishmania mexicana, LmmCRK1, is post-translationally regulated during the life cycle". J. Biol. Chem. 268(28):21044-21052 (1993).

Nyce, et al., "DNA antisense therapy for asthma in an animal model". Nature 385:721-725 (1997).

Oberbauer, "Not nonsense but antisense—Applications of Antisense Oligonucleotides in Different Fields of Medicine". Wein Klin. Wochenschr 109:40-46 (1997).

Ogg, et al., "Quantitation of HIV-1-Specific Cytotoxic T-Lymphocytes and Plasma Load of Viral RNA". Science 279:2103-2106 (1998).

Okada, et al., "Bone Marrow-Derived Dendritic Cells Pulsed With a Tumor-Specific Peptide Elicit Effective Anti-Tumor Immunity Against Intracranial Neoplasms". Int. J. Cancer 78:196-201 (1998).

Palucka, et al., "Dendritic Cells as the Terminal Stage of Monocyte Differentiation". J. Immunol. 160:4587-4595 (1999).

Papasavvas, et al., "Enhancement of Human Immunodeficiency Virus Type I-Specific CD4 and CD8 T Cell Responses in Chronically Infected Persons after Temporary Treatement Interruption". J. Infect. Diseases 182:766-775 (2000).

Pialoux, et al., "A Randomized Trial of Three Maintenance Regimens Given After Three Months of Induction Therapy with Zidovudine, Lamivudine, and Indinavie in Previously Untreated HIV-1-Infected Patients". The New England Journal of Medicine 339(18):1269-1276 (1998).

Piscitelli, "Immune-Based Therapies for Treatment of HIV Infection". The Annals of Pharmacotherapy 30:62-76 (1996).

Pisetsky, et al., "Immunological Properties of Bacterial DNA". Ann. NY Acad. Sci. 772:152-163 (1995).

Pisetsky, "Immunological consequences of nucleic acid therapy". Antisense Res. Dev. 5:219-225 (1995).

Pisetsky, "The immunological properties of DNA". J. Immunol. 156:421-423 (1996).

Pisetsky, et al., "Stimulation of murine lymphocyte proliferation by a phosphorothioate oligonucleotide with antisense activity for hepes simplex virus". Life Science 54:101-107 (1994).

Pisetsky, "Stimulation of in vitro proliferation of murine lymphocytes by synthetic oligodeoxyucleotides". Molecular Biol. Reports 18:217-221 (1993).

Plenat, "Animal models of antisense oligonucleotides: lessons for use in humans". J. Mol. Med. Today 2(6):250-257 (1996).

Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).

Quddus, et al., "Treating activated CD4+ T cells with either of two distinct DNA methyltransferase inhibitors, 5-azacytidine or procaniamide, is sufficient to cause a lupus-like disease in syngeneic mice". J. Clin. Invest. 92(1):38-53 (1993).

Ramanathan, et al., "Characterization of the Oligodeoxynucleotide-mediated Inhibition of Interferon-y-induced Major Histocompatibility Complex Class I and Intercellular Adhesion Molecule-1". The Journal of Biological Chemistry 269(40):24564-24574 (Oct. 1994).

Ramanathan, et al., "Inhibition of Interferon-y-Induced Major Histocompatibility Complex Class I Expression by Certain Oligodeoxynucleotides". Transplantation 57(4):612-615 (Feb. 1994).

Raz, "Deviation of the Allergic IgE to an IgG Response by Gene Immunotherapy". Int. Rev. Immunol. 18(3):271-289 (1999).

Raz, et al., "Preferential Induction of a Th1 Immune Response and Inhibition of Specific IgE Antibody Formation by Plasmid DNA Immunization". Proc. Natl. Acad. Sci. USA 93:5141-5145 (1996).

Raz, et al., "Intradermal gene immunization: the possible role of DNA uptake in the induction of cellular immunity to viruses". Proc. Natl. Acad. Sci. USA 91:9519-9523 (1994).

Ricci, et al., "T cells, cytokines, IgE and allergic airways inflammation". J. Invest. Allergol Clin. Immunol. 4(5):214-220 (1994).

Rojanasakul, "Antisense oligonucleotide therapeutics: drug delivery and targeting". Drug Delivery Reviews 18:115-131 (1996).

Roman, et al., "Immunostimulatory DNA sequences function as T helper-1-promoting aduvants". Nature Med. 3(8):849-854 (1997).

Rosenberg, et al., "Immune Control of HIV-1 After Early Treatment of Acute Infection". Nature 407:523-526 (2000).

Rosenberg, et al., "Vigorous HIV-1-Specific CD4+ T-Cell Responses Associated with Control of Viremia". Science 278:1447-1450 (1997).

Ruiz, et al., "Structured Treatment Interruption in Chronically HIV-1 Infected Patients After Long-Term Viral Suppression". AIDS 14:397-403 (2000).

Santini, et al., "Type I Interferon as a Powerful Adjuvant for Monocyte-derived Dendritic Cell Development and Activity in Vitro and in Hu-PBL-SCID Mice". J. Exp. Med. 191:1777-1788 (2000).

Sato, et al., "Immunostimulatory DNA sequences necessary for effective intradermal gene immunization". Science 273:352-354 (1996).

Scanlon, et al., "Oligonucleotide-mediated Modulation of Mammalian Gene Expression". FASEB J. 9:1288-1295 (1995).

Schnell, et al., "Identification and characterization of a *Saccharomyces cerevisiae* gene (PAR 1) conferring resistance to iron chelators". Eur. J. Biochem. 200:487-493 (1991).

Schoofs, "Small Steps—A Limited Experiment Opens New Approach in Fight Against HIV". Wall Street Journal (Sep. 28, 2000).

Schubbert, et al., "Ingested Foreign (phage M13) DNA Survives Transiently in the Gastrointestinal Tract and Enters the Bloodstream of Mice". Mol. Gen. Genet. 242:495-504 (1994).

Schwartz, et al., "Endotoxin responsiveness and grain dust-induced inflammation in the lower respiratory tract". Am. J. Physiol. 267(5):609-617 (1994).

Schwartz, et al., "The role of endotoxin in grain dust-induced lung disease". Am. J. Respir. Crit. Care Med. 152(2):603-608 (1995).

Schwartz, et al., "CpG motifs in bacterial DNA cause inflammation in the lower respiratory tract". J. Clin. Invest. 100(1):68-73 (1997).

Sedegah, et al., "Intertukin 12 induction of interferon g-dependent protection against malaria". Proc. Natl. Acad. Sci. USA 91:10700-10792 (1994).

Sethi, et al., "Postexposure prophytaxis against prion disease with a stimulator of innate immunity". Lancet 360:229-230 (2002).

Shafer, et al., "Highly Active Antiretroviral Therapy (HAART) for the Treatment of Infection With Human Immunodeficiency Virus Type 1". Biomed. & Pharmachther. 53:73-86 (1999).

Shirakawa, et al., "The inverse association between tuberculin responses and atopic disorder". Science 275(5296):77-79 (1997).

Sidman, et al., "γ-Interferon is one of several direct B cell-maturing lymphokines". Nature 309:801-804 (1984).

Sparwasser, et al., "Macrophages sense pathogens via DNA motifs: induction of tumor necrosis factor-alpha-mediated shock". Eur. J. Immunol. 27(7):1671-1679 (1997).

Sparwasser, et al., "Bacterial DNA and immunostimulatory CpG oligonuceotides trigger maturation and activation of murine dendritic cells". Eur. J. Immunol. 28:2045-2054 (1998).

Spiegelberg, et al., "Recognition of T Cell Epitopes and Lymphokine Secretion by Rye Grass Allergen Lolium perenne I-Specific Human T Cell Clones". J. of Immunology 152:4706-4711 (1994).

Stacey, et al., "Immunostimulatory DNA as an adjuvant in vaccination against Leishmania major". Infect. Immun. 67:3719-3726 (1999).

Stein, et al., "Oligodeoxynucleotides as inhibitors of gene expression: a review". Cancer Res. 48:2659-2668 (1998).

Stull, et al., "Antigene, ribozyme, and aptamer nucleic acid drugs: progress and prospects". Pharm. Res. 12(4):465-483 (1995).

Su, et al., "Vaccination against Chlamydial Genital Tract Infection after Immunization with Dendritic Cells Pulsed Ex Vivo with Nonviable Chlamydiae". J. Exp. Med. 188:809-818 (1998).

Subramanian, et al., "Theoretical considerations on the 'spine of hydration' in the minor groove of d(CGCGAATTCGCG) d(CGGCT-TAAGCGC): Monte Carlo computer simulation". Proc. Natl. Acad. Sci. USA 85:1836-1840 (1988).

Syme, et al., "Generation of Dendritic Cells ex vivo: Differences in Steady State versus Mobilized Blood from Patients with Breast Cancer, with Lymphoma, and from Normal Donors". J. Hematother. Stem Cell Res. 10:621-630 (2001).

Tanaka, et al., "An antisense oligonucleotide complementary to a sequence in I gamma 2b increases gamma 2b germhine transcripts, stimulates B cell DNA synthesis and inhibits immunoglobulin secretion". J. Exp. Med. 175:597-607 (1992).

Tarte, et al., "Extensive characterization of dendritic cells generated in serum-free conditions: regulation of soluble antigen uptake, apoptotic tumor cell phagocytosis, chemotaxis and T cell activation during maturation in vitro". Leukemia 14:2182-2192 (2000).

Thorne, "Experimental grain dust atmospheres generated by wet and dry aerosolization techniques". Am. J. Ind. Med. 25(1):109-112 (1994).

Tighe, et al., "Conjunction of Protein to Immunostimulatory DNA results in a Rapid Long-Lasting and Potent Induction of Cell-Mediated and Humoral Immunity". Eur. J. Immunol. 30:1939-1947 (2000).

Tokunaga, et al., "A synthetic single-stranded DNA, poly(dG, dC), induces interferon-α/β and -γ, augments natural killer activity and suppresses tumor growth". Jpn. J. Cancer Res. 79:682-686 (1988).

Tokunaga, et al., "Synthetic oligonucleotides with particular base sequences from the cDNA encoding proteins of Mycobacterium bovis BCG induce interferons and activate natural killer cells". Microbiol. Immunol. 36(1):55-66 (1992).

Uhlmann, et al., "Antisense oligonucleotides: a new therapeutic principle". Chem. Rev. 90:543-584 (1990).

Verdijk, et al., "Polyriboinosinic Polyribocytidylic Acid (Poly(I:C)) Induces Stable Maturation of Functionally Active Human Dendritic Cells". J. Immunol. 163:57-61 (1999).

Verma, et al., "Gene therapy—promises, problems and prospects". Nature 389:239-242 (Sep. 1997).

Verthelyi, et al., "Human Peripheral Blood Cells Differentially Recognize and Respond to Two Distinct CpG Motifs". J. Immunol. 166:2372-2377 (2001).

Verthelyi, et al., "CpG Oligodeoxynucleotides as Vaccine Adjuvants in Primates". J. Immunol. 168:1659-1663 (2002).
Vil'ner, "Effect of Amphotericin B on the interferonogenic activity of poly(G).poly (C) and poly(G,I).poly(C) in mice and their resistance to infection by the tick-borne encephalitis virus". Antibiotiki 27(11):827-830 (Nov. 1982), abstract.
Vil'ner, et al., "Effect of virazole on the antiviral activity of poly(G) X poly © and other polyribonucleotide interferongens". Antibiotiki 29(6):450-453 (1984), abstract.
Vil'Ner, et al., "Evaluation of the size of the continuous poly(G) site necessary for the biological activity of the poly(G).poly(C) complex". Vopr Virusol 30(3):337-340 (1985), abstract.
Vil'ner, "Effect of the size of the continuous poly(G) site in poly(G,A).poly(C) complexes on their interferon-inducing activity and their capacity to stimulate the development of the immunity". Vopr Virusol 31(6):697-700 (1986), abstract.
Vil'ner, et al., "Dependence of the antviral activity of the poly(G).poly(C) complex on the size of the continuous poly(C) segments". Vopr Virusol 33(3):331-335 (1988), abstract.
Wagner, "Bacterial CpG DNA Activates Immune Cells to Signal Infectious Danger". Adv. Immunol. 73:329-368 (1999).
Wagner, "Gene inhibition using antisense oligodeoxynucleotides". Nature 372:333-335 (1994).
Walker, et al., "Activated T Cells and Cytokines in Bronchoalveolar Lavages from Patients with Various Lung Diseases Associated with Eosinophilia". Am. J. Respir. Crit. Care Med. 150:1038-1048 (1994).
Walker, et al., "Immunostimulatory oligodeoxynucleotides promote protective immunity and provide systemic therapy for leishmaniasis via IL-12- and IFN-g-dependent mechanisms". Proc. Natl. Acad. Sci. USA 96:6970-6975 (1999).
Wallace, et al., "Oligonucleotide probes for the screening of recombinant DNA libraries". Methods Enzymol. 152:432-442 (1987).
Weiner, "The immunobiology and clinical potential of immunostimulatory CpG oligodeoxynucleotides". Leukocyte Bio. 68:455-463 (2000).
Weiner, et al., "Immunostimulatory oligodeoxynucleotides containing the CpG motif are effective as immune adjuvants in tumor antigen immunization". Proc. Natl. Acad. Sci. USA 94:10833-10837 (1997).
Weiss, "Upping the antisense ante: scientists bet on profits from reverse genetics". Science 139:108-109 (1991).
Whalen, et al., "DNA-Mediated Immunization to the Helatitis B Surface Antigen: Activation and Entrainment of the Immune Response". Ann. NY Acad. Sci. 772:64-76 (1995).
Whalen, "DNA vaccines for emerging infection diseases: what if?". Emerg. Infect. Dis. 2(3)168-175 (1996).
Wloch, et al., "The influence of DNA sequence on the immunostimulatory properties of plasmid DNA vectors". Hum. Gene Ther. 9(10):1439-1447 (Jul. 1998).
Woolridge, et al., "Immunostimulatory oligodeoxynucleotides containing CpG motifs enhance the efficacy of monoclonal antibody therapy of lymphoma". Blood 89:2994-2998 (1997).
Wu, et al., "Receptor-mediated gene delivery and expression in vivo". J. Biol. Chem. 263:14621-14624 (1988).
Wu-Pong, "Oligonucleotides: opportunities for drug therapy and research". Pharmaceutical Tech. 18:102-114 (1994).
Wyatt, et al., "Combinatorially selected guanosine-quartet structure is a potent inhibitor of human immundeficiency virus envelope-mediated cell fusion". Proc. Natl. Acad. Sci. USA 91:1356-1360 (Feb. 1994).

Yamamoto, et al., "Ability of oligonucleotides with certain palindromes to induce interferon production and augment natural killer cell activity is associated with their base length". Antisense Res. Dev. 4:119-123 (1994).
Yamamoto, "Unique palindromic sequences in synthetic oligonucleotides are required to induce inf and augment INF-mediated natural killer activity". J. Immunol. 148(12):4072-4076 (1992).
Yamamoto, et al., "In vitro augmentation of natural killer cell activity and production of interferonalpha/beta and -gamma with deoxyribonucleic acid fraction from Mycobacterium bovis BCG". Jpn. J. Cancer Res. 79:866-873 (1988).
Yamamoto, et al., "Synthetic oligonucleotides with certain palindromes stimulate interferon production of human peripheral blood lymphocytes in vitro". Jpn. J. Cancer Res. 85:775-779 (1994).
Yamamoto, et al., "Mode of action of oligonucleotide fraction extracted from Mycobacterium bovis BeG". Kekkaku 69(9):29-32 (1994).
Yamamoto, et al., "DNA from bacteria, but not vetebrates, induces interferons, activates natural killer cells, and inhibits tumor growth". Microbiol. Immunol. 36(9):983-997 (1992).
Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).
Yaswen, et al., "Effects of Sequence of Thioated Oligonucleotides on Cultured Human Mammary Epithelial Cells". Antisense Research and Development 3:67-77 (1993).
Yew, et al., "Contribution of Plasmid DNA to Inflammation in the Lung After Administration of Cationic Lipid: pDNA Complexes". Hum. Gene Ther. 10(2):223-234 (1999).
Yi, et al., "IFN-γ promotes IL-6 and lgM secretion in response to CpG motifs in bacterial DNA and oligonucleotides". J. Immunol. 156:558-564 (1996).
Yi, et al., "Rapid immune activation by CpG motifs in bacterial DNA". J. Immunol. 157:5394-5402 (1996).
Zelphati, et al., "Inhibition of HIV-1 Replication in Cultured Cells with Antisense Oligonucleotides Encapsulated in Immunoliposomes". Antisense Res. Dev. 3:323 (1993).
Zhang, et al., "Antigen- and Isotype-Specific Immune Responses to a Recombinant Antigen-Allergen Chimeric (RAAC) Protein". J. Immunol. 151:791-799 (1993).
Zhao, et al., "Comparison of cellular binding and uptake of antisense phosphodiester, phosphorothioate, and mixed phosphorothioate and methylphosphonate oligonucleotides". Antisense Res. Dev. 3(1):53-66 (1993).
Zhao, et al., "Stage-specific oligonucleotide uptake in murine bone marrow B-cell precursors". Blood 84(11):3660-3666 (1994).
Zheng, et al., "Contribution of Vascular Endothelial Growth Factor in the Neovascularization Process During the Pathogenesis of Herpetic Stromal Keratitis". J. Vriol. 75(20):9828-9835 (2001).
Zhu, et al., "Macaque blood-derived antigen-presenting cells elicit SIV-specific immune responses". J. Med. Primatol 29:182-192 (2000).
Zimmermann, et al., "CpG oligodeoxynucleotides trigger protective and curative Th1 responses in lethal murine leishmaniasis". J. Immunol. 160:3627-3630 (1998).

* cited by examiner

FIG. 1
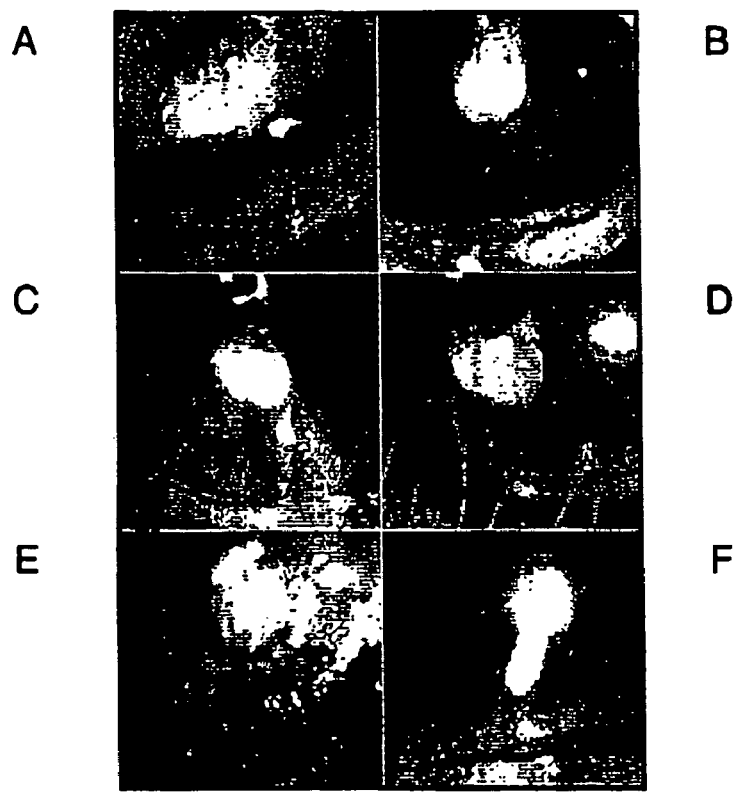
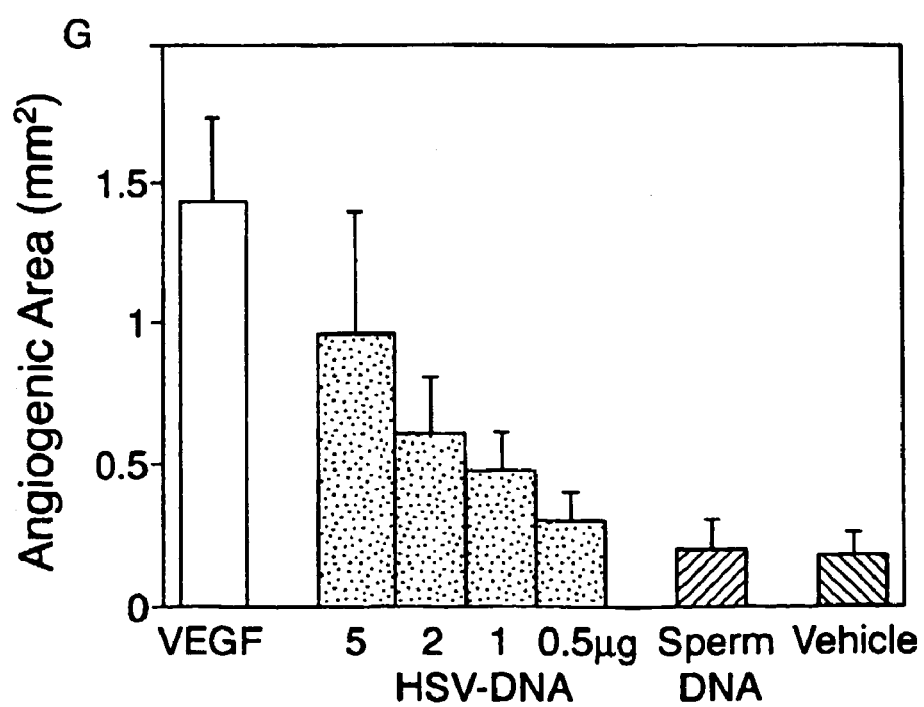

FIG. 2
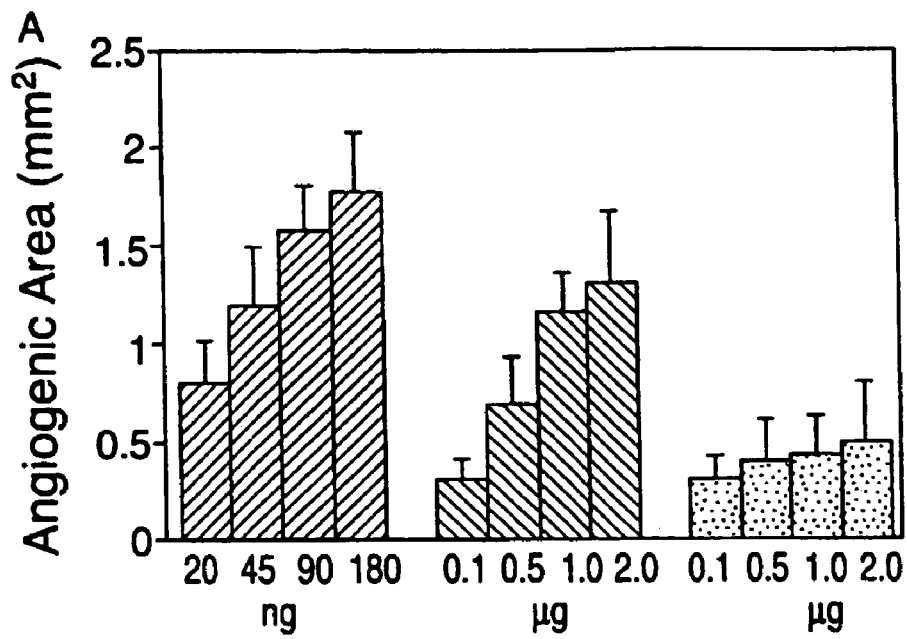
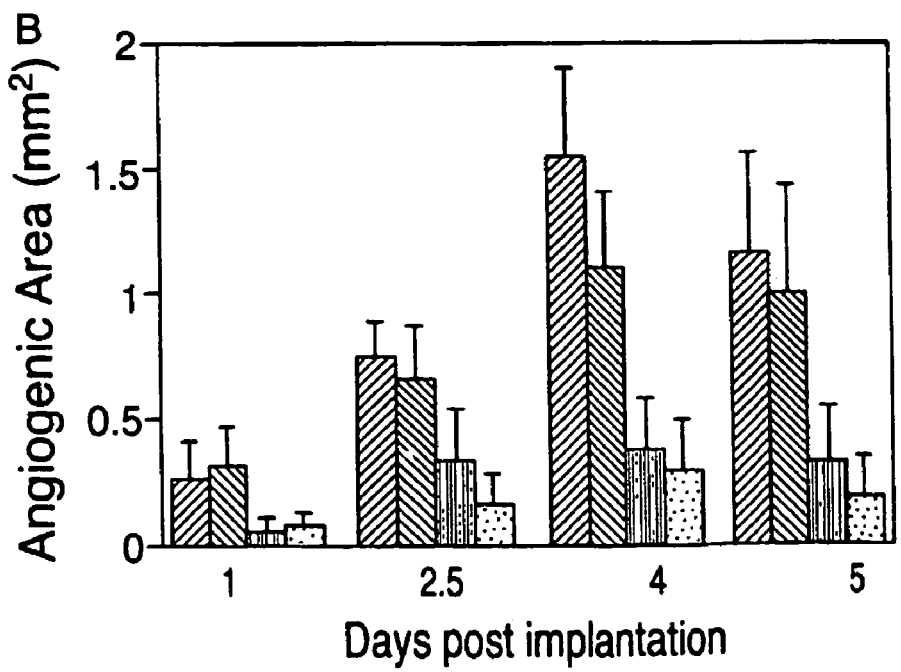

FIG. 3
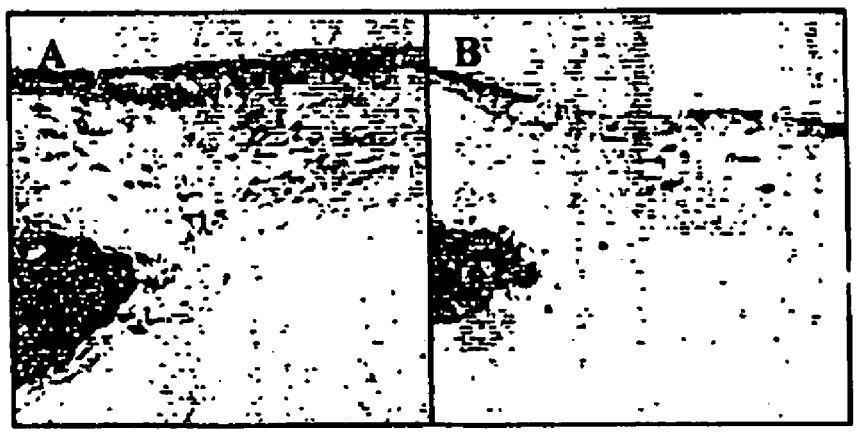
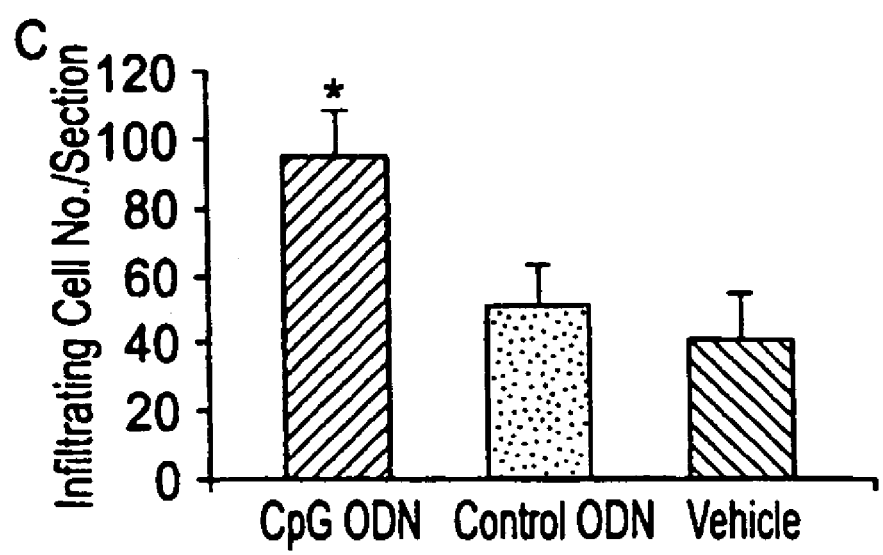

USE OF CPG OLIGODEOXYNUCLEOTIDES TO INDUCE ANGIOGENESIS

This is the § 371 U.S. National Stage of International Application No. PCT/US02/40955, filed Dec. 19, 2002, which was published in English under PCT Article 21(2), which in turn claims the benefit of U.S. Provisional Application No. 60/343,457, filed Dec. 20, 2001, which is incorporated by reference herein in its entirety.

FIELD

This application relates to the field of angiogenesis, more specifically to the use of CpG oligodeoxynucleotides to promote angiogenesis.

BACKGROUND

Angiogenesis, the process of developing a hemovascular network, is essential for the growth of solid tumors and is a component of normal wound healing and growth processes. It has also been implicated in the pathophysiology of atherogenesis, arthritis, corneal neovascularization, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. For example, Greenblatt et al., *J. Natl. Cancer Inst.* 41:111-124, 1968, concluded that tumor-induced neovascularization is mediated by a diffusible substance. Subsequently, a variety of soluble mediators have been implicated in the induction of neovascularization. These include prostaglandins (Auerbach, in Lymphokines, Pick and Landy, eds., 69-88, Academic Press, New York, 1981), human urokinase (Berman et al., *Invest. Opthalm. Vis. Sci.* 22:191-199, 1982), copper (Raju et al., *J. Natl. Cancer Inst.* 69:1183-1188, 1982), and various "angiogenesis factors" (e.g., see U.S. Pat. No. 4,916,073).

Angiogenesis factors play an important role in wound healing (Rettura et al., FASEB Abstract #4309, 61st Annual Meeting, Chicago, 1977) and likely play a role in the development of malignancies (Klagsburn et al., *Cancer Res.* 36:110-114, 1976; and Brem et al., *Science* 195:880-881, 1977), hence it would clearly be advantageous to identify new angiogenic agents.

DNA is a complex macromolecule whose activities are influenced by its base composition and base modification, as well as helical orientation. Bacterial DNA, as well as certain synthetic oligodeoxynucleotides (ODNs) containing umnethylated CpG sequences can induce proliferation and immunoglobulin production by murine B cells. Unmethylated CpG dinucleotides are more frequent in the genomes of bacteria and viruses than vertebrates. Recent studies suggest that immune recognition of these motifs may contribute to the host's innate immune response. (Klinman et al, *Proc. Natl. Acad. Sci.* USA 93:2879, 1996;. Yi et al, *J. Immun.* 157:5394, 1996; Liang et al, *J. Clin. Invest. II* 9:89, 1996; Krieg et al., *Nature* 374:546, 1995).

In mice, CpG DNA induces proliferation in almost all (>95%) of B cells and increases immunoglobulin secretion. This B-cell activation by CpG DNA is T-cell independent and antigen non-specific. In addition to its direct effects on B cells, CpG DNA also directly activates monocytes, macrophages, and dendritic cells to secrete a variety of cytokines. These cytokines stimulate natural killer (NK) cells to secrete γ-interferon (IFN-γ) and have increased lytic activity. However, although some of the effects of oligodeoxynucleotides containing unmethylated CpGs are known, many effects have yet to be elucidated.

SUMMARY

Methods of increasing angiogenesis are disclosed herein. The methods include administering an effective amount of a CpG oligodeoxynucleotide to increase angiogenesis.

For example, this disclosure provides a method of inducing production of vascular endothelial growth factor by a cell. The method includes contacting the cell with a CpG oligonulcleotide, thereby inducing the production of vascular endothelial growth factor by the cell.

The disclosure further provides a method of inducing neovascularization in a tissue. This method includes introducing a CpG oligodeoxynucleotide into an area of the tissue wherein the formation of new blood vessels is desired, thereby inducing neovascularization in the area of the tissue.

A method for screening for agents that inhibit neovascularization is also disclosed herein. The method includes administering a CpG oligodeoxynucleotide to a non-human mammal, and administering the agent to the non-human mammal. Inihibition of angiogenesis in the non-human mammal indicates that the agent may be effective in inhibiting neovascularization.

The foregoing and other features and advantages will become more apparent from the following detailed description of several embodiments, which proceeds with reference to the accompanying figures.

BRIEF DESCRIPTION OF THE FIGURES

FIG. 1 is a set of digital images demonstrating that HSV-DNA and CpG ODN induces angiogenesis. Representative 40×images are shown from day 4 post implantation. FIGS. 1A-F are digital images documenting angiogenesis induced by VEGF (FIG. 1A), vehicle alone (FIG. 1B), HSV DNA (FIG. 1C), herring sperm DNA (FIG. 1D), CpG ODN (FIG. 1E) and control ODN (FIG. 1E). Pellets containing 0.5-5 µg of HSV DNA or VEGF were implanted into corneal micropockets. The degree of neovascularization was compared to 5 µg of herring sperm DNA (4 mice/group). The mean angiogenic area from all samples is shown in FIG. 1G.

FIG. 2 shows the dose and kinetics of the angiogenic response to CpG DNA. FIG. 2A shows a dose-response of new blood vessel formation was monitored using the corneal micropocket assay 4 days post implantation. FIG. 2B shows the kinetics of neovascularization were measured 1-5 days post implantation. All results represent the mean of 4 animals/group.

FIG. 3 is a set of digital images showing that CpG DNA induces inflammation and VEGF expression in corneal micropockets. Pellets containing 1 µg of CpG or control ODN were implanted into mouse corneas. Frozen sections from these eyes were stained for VEGF expressing cells 4 days later. FIGS. 3A and 3B are digital images showing that positive cells are present in the ipsilateral site of the pellet implanted cornea. FIG. 3C is a bar graph of the number of infiltrating cells in the corneal stroma. Each number represented the mean total cellular infiltrates derived from 4 central corneal sections from two eyes. Magnification is 200×.

SEQUENCE LISTING

Figure 4:
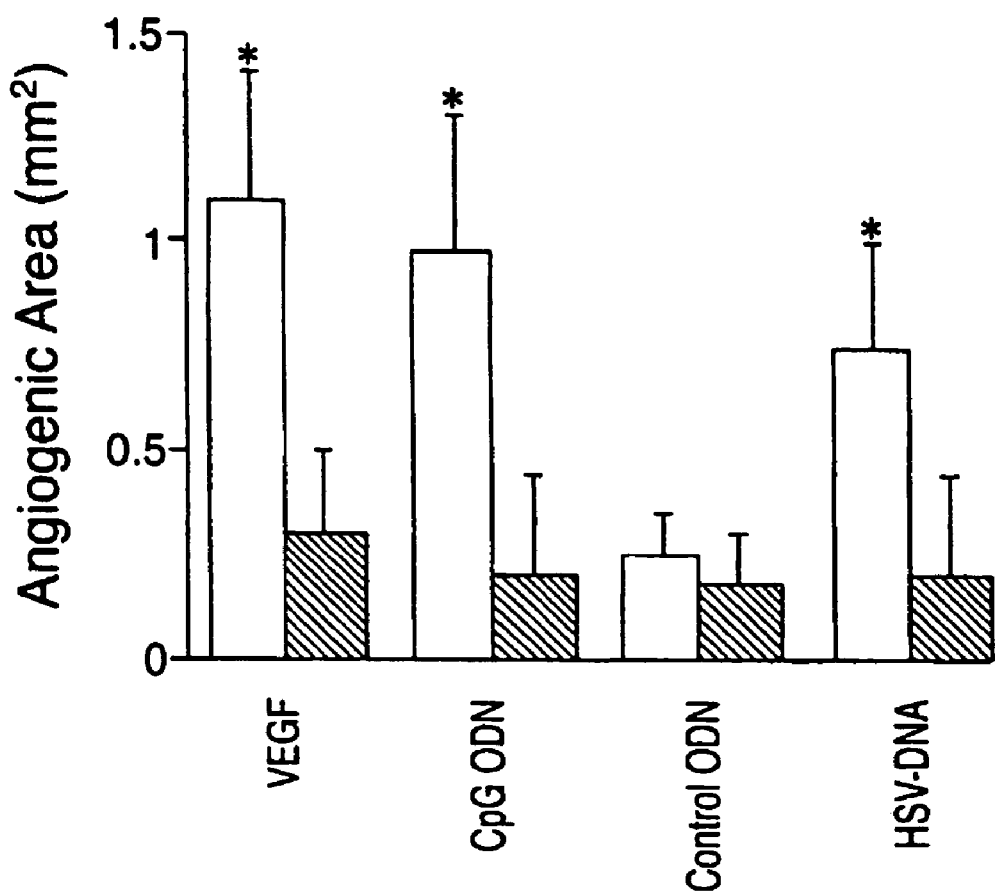
FIG. 4 is a bar graph showing HSV DNA and CpG ODN induced angiogenic responses react to anti-mVEGF antibody administration. The results demonstrated that anti-mVEGF antibody suppresses CpG DNA induced angiogenesis. Pellets containing 45 ng of rmVEGF164, 1 ug of ODN, or 2 ug of HSV or herring sperm DNA were placed in corneal pockets. Anti-mVEGF antibody (5 µg in 5 µl of PBS) was injected subconjunctivally into the eyes just prior to and 2 days after pellet implantation. The eyes were observed using stereomicroscopy, and neovascularization was measured in 4 mice/group. The solid black bar represents+anti-mVEGF Ab.

The nucleic and amino acid sequences listed in the accompanying sequence listing are shown using standard letter abbreviations for nucleotide bases, and three letter code for amino acids, as defined in 37 C.F.R. 1.822. In the accompanying sequence listing:

SEQ ID NOs: 1-4 are the nucleic acid sequences of K type CpG ODNs.

SEQ ID NO: 5 and SEQ ID NO: 6 are the nucleic acid sequence of D type CpG ODNs.

SEQ ID NO: 7 and SEQ ID NO: 8 are the nucleic acid sequences of exemplary angiogenic CpG ODNs.

SEQ ID NO: 9 is the nucleic acid sequence of an exemplary control (non-angiogenic) ODN.

SEQ ID NO: 10 and SEQ ID NO: 11 are the nucleic acid sequences of examples of primers that can be used to amplify VEGF nucleic acid.

SEQ ID NOs: 12-51 are the nucleic acid sequences of exemplary D ODN sequences and D ODN control sequences.

SEQ ID NOs: 52-106 are the nucleic acid sequences of exemplary K ODN sequences and K ODN control sequences.

DETAILED DESCRIPTION

I. Abbreviations
Ab: antibody
CpG ODN: an oligodeoxynucleotide (either a D or a K type) including a CpG motif, as defined herein.
HSV: Herpes Simplex Virus.
mm: millimeter
mRNA: messenger ribonucleic acid.
ODN: oligodeoxynucleotide
VEGF: vascular endothelial growth factor. Recombinant murine VEGF is indicated by "mVEGF" or rmVEGF." Recombinant human VEGF is indicated by "hVEGF" or "rhVEGF."
µg: microgram II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligodeoxynucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligodeoxynucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134. Amplification reactions can be used to produce CpG ODN, or can be used in the detection of MRNA, such as MRNA encoding a particular angiogenic faction (e.g. VEGF).

Animal: Living multi-cellular vertebrate organisms, a category that includes, for example, mammals and birds. The term mammal includes both human and non-human mammals. Similarly, the term "subject" includes both human and veterinary subjects.

Angiogenesis: Process leading to the generation of new blood vessels through sprouting from already existing blood vessels. The process involves the migration and proliferation of endothelial cells from preexisting vessels. Angiogenesis occurs both during pre-natal development, post-natal development, and in the adult. In the adult, angiogenesis occurs during the normal cycle of the female reproductive system, wound healing, and during pathological processes such as cancer (for review see Battegay, *J. Molec. Med.* 73(7):333-

346, 1995; Beck and D'Amore, *FASEB J.* 11(5):365, 1997). "Neovascularization" is development of new blood vessels in a tissue.

Angiogenic Factor: A molecule that promotes angiogenesis. A plethora of experiments have suggested that tissues secrete factors which promote angiogenesis under conditions of poor blood supply during normal and pathological angiogenesis processes. Angiogenic molecules are generated by tumor, inflammatory, and connective tissue cells in response to hypoxia and other as yet ill-defined stimuli. The first indication of the existence of such diffusible substances was gleaned from filtration experiments demonstrating that tumor cells separated from underlying tissues by filters that do not allow passage of cells are nevertheless capable of supporting vessel growth in these tissues. The formation of blood vessels is initiated and maintained by a variety of factors secreted either by the tumor cells themselves or by accessory cells. Many different growth factors and cytokines have been shown to exert chemotactic, mitogenic, modulatory or inhibitory activities on endothelial cells, smooth muscle cell and fibroblasts and can, therefore, be expected to participate in an angiogenic process in one way or another. For example, factors modulating growth, chemotactic behavior and/or functional activities of vascular endothelial cells include aFGF, bFGF, angiogenein, angiotropin, epithelial growth factor, IL-8, and vascular endothelial growth factor (VEGF), amongst others.

As many angiogenic factors are mitogenic and chemotactic for endothelial cells their biological activities can be determined in vitro by measuring the induced migration of endothelial cells or the effect of these factor on endothelial cell proliferation. Alternatively, a bioassay may be utilized for direct determination of angiogenic activities and permit repeated, long-term quantitation of angiogenesis as well as physiological characterization of angiogenic vessels. Many such assays are known in the art.

One assay employs the use of a non-vascularized mouse eye (e.g. Kenyon et al., *Invest Opthalmol. Vis. Sci.* 37:625, 1996; also see Examples section) or the rabbit eye (e.g., see Gaudric et al. *Ophthal. Res.* 24:181, 1992)., and is termed a cornea pocket assay. This assay has the advantage that new blood vessels are easily detected and essentially must be newly formed blood vessels in the normally avascular cornea. Another assay involves the use of chicken chorioallantoic membrane (the CAM assay; see Wilting et al., *Anat. Embryol.* 183:259, 1991). Other assays in the rat, such as the rat aortic ring model, provide reproducible assays that are often utilized to identify angiogenic agonists and antagonists (e.g. see Lichtenberg et al., *Pharmacol Toxicol.* 84:34, 1999).

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG oligodeoxynucleotide is an oligodeoxynucleotide that is at least about ten nucleotides in length and includes an unmethylated CpG. CpG oligodeoxynucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

D Type Oligodeoxynucleotide (D ODN): An oligodeoxynucleotide including an unmethylated CpG motif that has a sequence represented by the formula:

5' RY-CpG-RY 3' wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by the following formula:

5'-$N_1N_2N_3 R_1 Y_2$ CpG $R_3 Y_4 N_4N_5N_6(N)_x(G)_z$-3' (SEQ ID NO: 6)

wherein the central CpG motif is unmethylated, R is a purine nucleotide, Y is a pyrimidine nucleotide, N is any nucleotide, X is any integer from 0 to 10, and Z is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular response.

Herpes Virus: There are eight known herpesviruses which are divided into three classes, denoted alpha, beta, and gamma. The herpesviruses include human herpesviruses 1, human herpes virus 2, varicella zoster virus, human cytomegalovirus, Epstein BarR virus, mouse cytomegalovirus, and human herpesvirus 8, amongst others. The structure of the herpesvirus particle is very complex. The core consists of a toroidal shape with the large DNA genome wound around a proteinaceous core. The complex capsid surrounds the core. Outside the capsid is the tegument, a protein-filled region which appears amorphous in electron micrographs. On the outside of the particle is the envelope, which contains numerous glycoproteins.

All herpesvirus genomes have a unique long (UL) and a unique short (US) region, bounded by inverted repeats. The repeats allow rearrangements of the unique regions and herpesvirus genomes exist as a mixture of 4 isomers. Herpesvirus genomes also contain multiple repeated sequences and depending on the number of these, genome size of various isolates of a particular virus can vary by up to 10 kbp.

The prototype member of the family is Herpes Simplex Virus (HSV) which is about 160 kbp in length. The complete sequence of HSV is known. There are two antigenic types, HSV-1 and HSV-2, which share antigenic cross-reactivity but different neutralization patterns and tend to produce different clinical symptoms. Man is believed to be the natural host for HSV, but the virus is also capable of infecting various animals, including rodents.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

5' $N_1N_2N_3$D-CpG-W$N_4N_5N_6$ 3'    (SEQ ID NO: 1)

wherein the central CpG motif is unmethylated, D is T, G or A, W is A or T, and $N_1$, $N_2$, $N_3$, $N_4$, $N_5$, and $N_6$ are any nucleotides. In one embodiment, D is a T. Additional detailed description of K ODN sequences and their activities can be found in the description below. Generally K ODNs can stimulate a humoral response. For example, K ODNs stimulate the production of imnmunoglobulins, such as IgM and IgG. K ODNs can also stimulate proliferation of peripheral blood mononuclear cells and increase expression of IL-6 and/or IL-12, amongst other activities.

Mammal: This term includes both human and non-human mammals.

Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA, oligodeoxynucleotides or RNA, oligoribonucleotides) which is at least six nucleotides, for example at least 10, 15, 50, 100 or even 200 nucleotides long.

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence. In one embodiment, CpG ODN stimulates (e.g. has a mitogenic effect or induces cytokine production) vertebrate immune cells. CpG ODN can also stimulate angiogenesis. The cytosine, guanine is unmethylated.

An "oligonucleotide delivery complex" is an oligonucleotide associated with (e.g. ionically or covalently bound to; or encapsulated within) a targeting means (e.g. a molecule that results in a higher affinity binding to a target cell (e.g. B cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Generally, the complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence, if the promoter affects the transcription or expression of the coding sequence. Generally, operably linked DNA sequences are contiguous and, where necessary to join two protein coding regions, in the same reading frame.

Pharmaceutical agent or drug: A chemical compound, nucleic acid molecule, or composition capable of inducing a desired therapeutic or prophylactic effect when properly administered to a subject. In one embodiment, a pharmaceutical agent induces angiogenesis or the production of VEGF.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the oligodeoxynucleotides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleic acid sequence of any length. Therefore, a polynucleotide includes molecules which are 10, 15, 50, 100, 200 (oligonucleotides) and also nucleotides as long as a full length cDNA.

Portion (of a Nucleotide Sequence): At least 10, or 20, 30 or 40 nucleotides, in some cases, it would be advantageous to use a portion comprising 50 or more contiguous nucleotides of that specified nucleotide sequence (but no more than about a kilobase). A portion as used herein may includes a whole gene or a whole specified sequence, e.g., a portion of the DNA sequence of gene, or a portion of the DNA sequence of a virus. A portion may include as few as 10 nucleotides, or as many as 50 nucleotides or more, or a whole open reading frame, or the an entire gene of a viral genome, so long as the sequence comprises at least 10 nucleotides of the DNA sequence.

Purified: The term purified does not require absolute purity; rather, it is intended as a relative term. Thus, for example, a purified oligonucleotide preparation is one in which the oligodeoxynucleotide is more enriched than the protein is in its generative environment, for instance within a cell or in a biochemical reaction chamber. Preferably, a preparation of oligodeoxynucleotide is purified such that the oligodeoxynucleotide represents at least 50% of the total nucleotide content of the preparation.

Therapeutically effective dose: A dose sufficient to induce angiogenesis, or promote production of VEGF. In one embodiment, a therapeutically effective dose is an amount sufficient to relieve symptoms caused by the disease (e.g. atherosclerosis) or is sufficient to promote survival of a graft or cells transplanted into a subject.

Vascular Endothelial Growth Factor (VEGF): VEGF is a homodimeric heavily glycosylated protein of 46-48 kDa (24 kDa subunits). Glycosylation is not required, however, for biological activity. The subunits are linked by disulphide bonds. The human factor occurs in several molecular variants of 121 (VEGF-121), 165 (VEGF-165), 183 (VEGF-183), 189 (VEGF-189), 206 (VEGR-206) amino acids, arising by alternative splicing of the MRNA (for review see Neufeld et al., *FASEB J.* 13:9, 1999)

The human gene encoding VEGF has a length of approximately 12 kb and contains eight exons. Four species of MRNA encoding VEGF have been identified and found to be expressed in a tissue-specific manner. They arise from differential splicing with the 165 amino acid form of VEGF lacking sequences encoded by exon 6 and the 121 amino acid form lacking exon 6 and 7 sequences. The VEGF gene maps to human chromosome 6p12-p21.

VEGF is a highly specific mitogen for vascular endothelial cells. In vitro the two shorter forms of VEGF stimulate the proliferation of macrovascular endothelial cells. VEGF does not appear to enhance the proliferation of other cell types. VEGF significantly influence vascular permeability and is a strong angiogenic protein in several bioassays and probably also plays a role in neovascularization under physiological conditions. A potent synergism between VEGF and beta-FGF in the induction of angiogenesis has been observed. It has been suggested that VEGF released from smooth muscle cells and macrophages may play a role in the development of arteriosclerotic diseases.

VEGF can be assayed by an immunofluorometric test. An alternative and entirely different detection method is RT-PCR quantitation of cytokines. Methods for performing these assays are known (e.g. see Yeo et al., *Clinical Chem.* 38:71, 1992);

CpG ODN

A CpG oligodeoxynucleotide is an oligodeoxynucleotide including a CpG motif, wherein the pyrimdine ring of the cytosine is unmethylated. Two types of CpG ODNs have been identified: K type and D type ODNs. In one embodiment, the CpG ODN is in the range of about 8 to 30 bases in size. In another embodiment, the CpG ODN is at least 10 bases in size. For use in the methods disclosed herein, the nucleic acids can be synthesized de novo using any of a number of procedures well known in the art. For example, the b-cyanoethylphosphoramidite method (Beaucage et al., *Tet. Let.* 22:1859, 1981) or the nucleoside H-phosphonate method (Garegg et al., *Tet. Let.* 27:4051, 1986; Froehleret al., *Nucl. Acid Res.* 14:5399, 1986; Garegg et al., *Tet. Let.* 27:4055, 1986; Gaffiey et al., *Tet. Let.* 29:2619, 1988) can be utilized. These chemistries can be performed by a variety of automated oligonucleotide synthesizers available in the market.

Alternatively, CpG dinucleotides can be produced on a large scale in plasmids, (see Sambrook, et al., *Molecular Cloning: A Laboratory Manual*, Cold Spring Harbor Laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases (PCT/US98/03678).

For use in vivo, nucleic acids can be utilized that are relatively resistant to degradation (e.g., via endo-and exo-nucleases). Secondary structures, such as stem loops, can stabilize nucleic acids against degradation. Alternatively, nucleic acid stabilization can be accomplished via phosphate backbone modifications. In one embodiment, a stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made (e.g., as described in U.S. Pat. No. 4,469,863) and alkylphosphotriesters (in which the charged oxygen moiety isalkylated, as described in U.S. Pat. No. 5,023,243 and European Patent No. 092,574), and can be prepared by automated solid phase synthesis using commercially available reagents.

In one embodiment, the phosphate backbone modification occurs at the 5' end of the nucleic acid. One specific, non-limiting example of a phosphate backbone modification is at the first two nucleotides of the 5' end of the nucleic acid. In another embodiment, the phosphate backbone modification occurs at the 3' end of the nucleic acid. One specific, non-limiting example of a phosphate backbone modification is at the last five nucleotides of the 3' end of the nucleic acid.

Methods for making other DNA backbone modifications and substitutions have been described (Uhlmann et al., *Chem. Rev.* 90:544, 1990; Goodchild, *Bioconjugate Chem.* 1:1, 1990). 2'-O-methyl nucleic acids with CpG motifs also cause angiogenesis, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (e.g., an endothelial cell) surfaces and/or increased cellular uptake by target cells to form a "nucleic acid delivery complex." Nucleic acids can be ionically or covalently associated with appropriate molecules using techniques which are well known in the art (see below). Nucleic acids can alternatively be encapsulated in liposornes or virosomes using well-known techniques.

D and K type nucleic acids sequences of use are described in the published PCT Applications No. WO 98/18810A1 (K-type) and WO 00/61151 (D-type), which are incorporated by reference herein in their entirety.

A CpG ODN can be associated with (e.g., ionically or covalently bound to, or encapsulated within) a targeting moiety. Targeting moieties include any a molecule that results in higher affinity binding to a target cell, such as, but not limited to, an endothelial cell.

A variety of coupling or cross-linking agents can be used to form the delivery complex, such as protein A, carbodianide, and N-succinimidyl (2-pyridyldithio) propionate (SPDP). Examples of delivery complexes include CpG ODNs associated with a sterol (e.g., cholesterol), a lipid (e.g., a cationic lipid, virosome or liposome), and a target cell specific binding agent (e.g., a ligand recognized by target cell specific receptor). In one embodiment, the complexes are sufficiently stable in vivo to prevent significant uncoupling prior to internalization by the target cell. However, these complexes can be cleavable under appropriate circumstances such that the oligodeoxynucleotide can be released in a functional form (see WO 00/61151).

In another embodiment, fragments of viral or bacterial DNA can be used to produce CpG ODN, and thus to promote angiogenesis, and/or to induce the secretion of VEGF. Suitable DNA includes, but is not limited to, herpesviral DNA, such as HSV-1 or HSV-2 DNA. In one embodiment, fragmented Herpes Simplex Virus DNA is utilized as CpG ODNs. Specific non-limiting examples of fragmented viral DNA include, but are not limited to, viral DNA with an average length of ten bases, viral DNA with an average length of 100 bases, and viral DNA with an average length of 500 bases.

K ODN

In one embodiment, the CpG ODN is a K type ODN. Briefly, the K type nucleic acid sequences useful in the methods disclosed herein are represented by the formula:

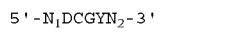            (SEQ ID NO: 2)

wherein at least one nucleotide separates consecutive CpGs; D is adenine, guanine, or thymidine; Y is cytosine or thymine, N is any nucleotide and $N_1+N_2$ is from about 0-26 bases. In one embodiment, $N_1$ and $N_2$ do not contain a CCGG quadmer or more than one CGG trimer; and the nucleic acid sequence is from about 8-30 bases in length. However, nucleic acids of any size (even many kb long) can be used in the methods disclosed herein if CpGs are present. In one embodiment, synthetic oligonucleotides of use do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs). An exemplary nucleic acid sequence is:

```
5'-ATAATCGACGTTCAAGCAAG-3'.      (SEQ ID NO: 3)
```

In another embodiment, the method of the invention includes the use of an oligodeoxynucleotide which contains a CpG motif represented by the formula:

```
5'-N₁RDCGYTN₂-3'        (SEQ ID NO: 4)
``` wherein at least one nucleotide separates consecutive CpGs; RD is selected from the group consisting of GpT, GpG, GpA, ApT and ApA; YT is selected from the group consisting of TpT or CpT; N is any nucleotide and $N_1+N_2$ is from about 0-26 bases.

In one embodiment, $N_1$, and $N_2$ do not contain a CCGG quadmer or more than one CCG or CGG trimer. CpG ODN are also in the range of 8 to 30 bases in length, but may be of any size (even many kb long) if sufficient motifs are present. In one embodiment, synthetic oligodeoxynucleotides of this formula do not include a CCGG quadmer or more than one CCG or CGG trimer at or near the 5' and/or 3' terminals and/or the consensus CpG motif is not a palindrome. Other CpG oligodeoxynucleotides can be assayed for efficacy using methods described herein. It should be noted that exemplary K-type oligodeoxynucleotides are known in the art, and have been fully described, for example in WO 98/18810A1.

D ODN

In another embodiment, the CpG ODN is a "D type" CpG ODN (see Verthelyi et al, *J. Immunol.* 166:2372, 2001; published PCT Application No. WO 00/61151, both of which show sequences of representative D ODN, and both of which are herein incorporated by reference in their entirety). In one embodiment, a "D type" CpG ODN comprises multiple different CpG sequences with at least one of the multiple different CpG sequences represented by the formula:

```
5' N₁N₂N₃T-CpG-WN₄N₅N₆ Y,      (SEQ ID NO: 5)
``` wherein W is A or T, and $N_1$, $N_2$, $N_3$ $N_4$, $N_5$, and $N_6$ are any nucleotides or the formula 5' RY-CpG-RY T, wherein R is A or G and Y is C or T.

Alternatively, different sequences can be represented by the formula:

```
5' RY-CpG-RY-3'
``` wherein R is A or G and Y is C or T.

In one embodiment, a D type ODN is at least about 16 nucleotides in length and includes a sequence represented by the following formula:

```
5'-N₁N₂N₃ R₁ Y₂ CpG R₃ Y₄ N₄N₅N₆(N)ₓ      (SEQ ID NO: 6)
(G)_z-3'
``` wherein the central CpG motif is unmethylated, R is a purine nucleotide, Y is a pyrimidine nucleotide, N is any nucleotide, X is any integer from 0 to 10, and Z is any integer from 4 to 10.

The region $R_1$ $Y_2$ CpG $R_3$ $Y_4$ is termed the CpG motif. The region $N_1N_2N_3$ is termed the 5' flanking region, and the region $N_4N_5N_6$ is termed the 3' flanking region. If nucleotides are included 5' of $N_1N_2N_3$ in the D ODN these nucleotides are termed the 5' far flanking region. Nucleotides 3' of $N_4N_5N_6$ in the D ODN are termed the 3' far flanking region.

In one specific non-limiting example, $Y_2$ is a cytosine. In another specific, non-limiting example, $R_3$ is a guanidine. In yet another specific, non limiting example, $Y_2$ is a thymidine and $R_3$ is an adenine. In a further specific, non-limiting example, $R_1$ is an adenine and $Y_2$ is a tyrosine. In another specific, non-limiting example, $R_3$ is an adenine and $Y_4$ is a tyrosine.

In one specific not limiting example, Z is from about 4 to about 8. In another specific, non-limiting example, Z is about 6.

D-type CpG oligodeoxynucleotides can include modified nucleotides. Without being bound by theory, modified nucleotides can be included to increase the stability of a D-type oligodeoxynucleotide. Without being bound by theory, because phosphorothioate-modified nucleotides confer resistance to exonuclease digestion, the D ODN are "stabilized" by incorporating phosphorothioate-modified nucleotides. In one embodiment, the CpG dinucleotide motif and its immediate flanking regions include phosphodiester rather than phosphorothioate nucleotides. In one specific non-limiting example, the sequence $R_1$ $Y_2$ CpG $R_3$ $Y_4$ includes phosphodiester bases. In another specific, non-limiting example, all of the bases in the sequence $R_1$ $Y_2$ CpG $R_3$ $Y_4$ are phosphodiester bases. In yet another specific, non-limiting example, $N_1N_2N_3$ and $N_4N_5N_6(N)_x(G)_z$ include phosphodiester bases. In yet another specific, non-limiting example, $N_1N_2N_3$ $R_1$ $Y_2$ CpG $R_3$ $Y_4$ $N_4N_5N_6(N)_x$ $(G)_z$ include phosphodiester bases. In further non-limiting examples, the sequence $N_1N_2N_3$ includes at most one or at most two phosphothioate bases and/or the sequence $N_4N_5N_6$ includes at most one or at most two phosphotioate bases. In additional non-limiting examples, $N_4N_5N_6(N)_x$ $(G)_z$ includes at least 1, at least 2, at least 3, at least 4, or at least 5 phosphothioate bases. Thus, a D type oligodeoxynucleotide can be a phosphorothioate/phosphodiester chimera.

Any suitable modification can be used to render the D oligodeoxynucleotide resistant to degradation in vivo (e.g., via an exo- or endo-nuclease). In one specific, non-limiting example, a modification that renders the oligodeoxynucleotide less susceptible to degradation is the inclusion of non-traditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D type oligodeoxynucleotides can also be modified to contain a secondary structure (e.g., stem loop structure). Without being bound by theory, it is believed that incorporation of a stem loop structure renders an oligodeoxynucleotide more effective.

In a further embodiment, $R_1\,Y_2$ and $R_3\,Y_4$ are self complementary. In another embodiment, $N_1N_2N_3$ and $N_4N_5N_6$ are self complementary. In yet another embodiment, $N_1N_2N_3\,R_1\,Y_2$ and $R_3\,Y_4\,N_4N_5N_6$ are self complementary.

Specific non-limiting examples of a D type oligodeoxynucleotide wherein $R_1\,Y_2$ and $R_3\,Y_4$ are self complementary include, but are not limited to, ATCGAT, ACCGGT, ATCGAC, ACCGAT, GTCGAC, or GCCGGC. Without being bound by theory, the self complementary base sequences can help to form a stem-loop structure with the CpG dinucleotide at the apex to facilitate immunostimulatory functions. Thus, in one specific, non-limiting example, D type oligodeoxynucleotides wherein $R_1\,Y_2$ and $R_3\,Y_4$ are self-complementary induce higher levels of IFN-γ production from a cell of the immune system (see below). The self complementary need not be limited to $R_1\,Y_2$ and $R_3\,Y_4$. Thus, in another embodiment, additional bases on each side of the three bases on each side of the CpG-containing hexamer form a self complementary sequence (see above).

It should be noted that exemplary D type oligodeoxynucleotides are well known in the art, for example as described in WO 00/61151.

Pharmacologic Compositions and Therapeutic Use

CpG ODNs can be used to promote angiogenesis and/or to induce production of an angiogenic factor, in vivo or in vitro. In one embodiment, the factor is a factor modulating growth, chemotactic behavior and/or a functional activity of vascular endothelial cells. Specific, non-limiting examples of angiogenic factors include, but are not limited to, aFGF, bFGF, angiogenein, angiotropin, epithelial growth factor, IL-8, and vascular endothelial growth factor (VEGF), amongst others. For example, CpG ODN is used to induce the production of VEGF, and/or promote angiogenesis.

In one embodiment, a CpG ODN is administered to a cell or a tissue culture in vitro. In another embodiment, cells or a tissue treated with CpG ODN are transplanted into a subject. In one specific, non-limiting example, CpG ODNs are administered to a graft, such as a skin graft, prior to transplantation. In one specific, non-limiting example, CpG ODNs are administered to an organ, such as a heart, lung, or kidney, prior to transplantation.

In one embodiment, the CpG ODN is administered with a second angiogenic factor. Specific, non-limiting examples of angiogenic factors of use include, but are not limited to aFGF, bFGF, platelet derived endothelial cell growth factor, angiogenein, angiotropin, epithelial growth factor, and IL-8.

In another embodiment, CpG ODN are utilized in vivo. Thus, a therapeutically effective amount of a CpG ODN and a pharmacologically acceptable carrier are administered to a subject, such that cells of the subject produce VEGF. In addition, a therapeutically effective amount of a CpG ODN and a pharmacologically acceptable carrier can be administered to a subject to promote angiogenesis. Suitable subjects include, but are not limited to, subjects with a graft (e.g., a skin graft), subjects who exhibit male pattern baldness, or subjects who have a wound, in order to promote wound healing. Suitable subjects also include those with atherosclerosis. Additional agents that promote angiogenesis are known in the art, and can be administered in conjunction with a CpG ODN.

Additional applications for in vivo use include vascularization of ischemic tissue such as ischemic heart tissue and ischemic peripheral tissue, and vascularization of chronic wounds, burns and transplanted tissue. In one example, the CpG ODN is administered (either systemically or locally) to a subject undergoing transmyocardial laser revascularization. In yet other examples, the CpG ODN are administered to animals to promote inappropriate neovascularization to provide an animal model of inappropriate neovascularization (see below and see Example 1). The animal model then can be used to study treatments to induce regression of vascularization (such as the administration of potential drugs to induce regression of pathological neovascularization).

Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of CpG ODN, both in vivo and ex vivo, to promote angiogenesis and/or induce the production of VEGF. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the active ingredient can be combined with carriers suitable for incorporation into tablets, pills, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the ODN can be contained within or conjugated with a protein, hydrocarbon or lipid, whether for in vitro or in vivo administration. Once this molecule is administered, the ODN sequence must be exposed on the surface to induce production of VEGF and/or angiogenesis. The CpG ODN can also be co-administered with a protein, hydrocarbon, or lipid. Co-administration can be such that the CpG ODN is administered before, at substantially the same time as, or after the protein, hydrocarbon, or lipid. In one embodiment, the ODN is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the compositions of the invention is contained in a form within a matrix such as those described in U.S. Pat. Nos. 4,452,775; 4,667,014; 4,748,034; 5,239,660; and 6,218,371 and (b) difusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as to promote graft survival or to treat baldness. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with CpG ODNs (see U.S. Pat. No. 6,218,371). For use in vivo, nucleic acids are preferably relatively resistant to degradation (e.g. via endo- and exo-nucleases). Thus, modifications, such as phosphate backbone modifications (see above) can be utilized to promote stabilization.

Screening Methods

A method is provided herein for screening for an agent that inhibit neovascularization. The method includes administering a CpG ODN to a non-human mammal. The animal can be any mammal, including, but not limited to, mice, rats, or rabbits. However, the use of any veterinary animal is contemplated, including both domestic (e.g., cats, dogs, guinea pigs, hamsters, etc.) and farm (e.g. cows, sheep, pigs, etc.) is contemplated. In one embodiment, the CpG ODN is administered to the cornea. However, administration can be to any tissue where angiogenesis can be assessed.

The method also includes administering a potentially therapeutically effective amount of the agent to the non-human mammal. Suitable agents include, but are not limited to, peptides, cytokines, chemokines, small molecules, chemical compounds, known pharmaceutical agents, afitisense molecules, ribozymes, or any other molecules of interest. Inhibition of angiogenesis in the non-human animal indicates that the agent is effective in inhibiting neovascularization.

In one specific, non-limiting example, angiogenesis in the non-human animal treated with the agent is compared to a control. Suitable controls include, but are not limited to angiogenesis in a non-human animal treated with the CpG ODN, but not treated with the agent. Suitable controls also include a standard value, or an non-human animal treated with the CpG ODN, and treated with an agent know to inhibit angiogenesis.

The invention is illustrated by the following non-limiting Examples.

EXAMPLES

Example 1

Materials and Methods

Reagents

Phosphorothioate ODNs were synthesized at the Center for Biologics Evaluation and Research core facility, as previously described (Verthelyi et al., *J Immunol.*, 166:2372-2377, 2001). The sequences of the stimulatory ODNs used in this study were: ODN 1466, having the sequence TCAACGT-TGA (SEQ ID NO: 7) and ODN 1555 having the sequence GCTAGACGTTAGCGT. (SEQ ID NO: 8). The control ODN 1471 had the sequence TCAAGCTTGA (SEQ ID NO: 9). There was no detectable endotoxin contamination in any of the ODNs, as monitored by LAL assay (Bio Whittaker, Inc., Walkersville, Md.). In some experiments, FITC was conjugated to the 5' end of these ODNs to monitor their distribution in vivo.

Herring sperm DNA (Boehringer Mannheim, Mannheim, Germany) was prepared by passage through Detoxi-Gel™ Endotoxin Removal Gel 20344 (PcPierce, Rockford, Ill.) to reduce endotoxin levels to <6 EU/mg. Recombinant human VEGF165 (rhVEGF), recombinant mouse VEGF (rm-VEGF), mouse VEGF neutralizing antibody and biotinylated rat-anti-mouse VEGF were purchased from R & D Systems Inc. (Minneapolis, Minn.). Synthetic mesh and hydron polymer (type NCC) were purchased from Sefar America Inc. (Kansas City, Mo.) and Hydro Med Sciences, respectively. Sucralfate was provided by Bulch Meditec (Vaerlose, Denmark). Lipopolysacharride (LPS) was purchased from Sigma (St. Louis, Mo.) and streptavidin-PE from Pharmingen (San Diego, Calif.).

Isolation of HSV-1 DNA

Virus was harvested from infected Vero cells when the cytopathic effects were maximal by centrifugation at 1000 g for 30 minutes at 4° C. (Klinman et al., *Proc Natl Acad Sci USA*, 93:2879-83, 1996). Cells were suspended in sterile PBS and freeze-thawed three times to release viral particles. The virion-containing supernatant was then ultracentrifuged at 25,000 g for 90 minutes at 4° C., and the pellet suspended in sterile phosphate buffered saline (PBS). Viral particles were precipitated in a solution of 7% polyethylene glycol 8000 in 2.3% NaCl overnight at 4° C. DNA was isolated from virions by treatment with 200 ug/ml proteinase K and 1% sarcosyl in STE buffer overnight at 56° C. The DNA was purified by multiple phenol:chloroform:isoamyl alcohol extractions, precipitated, dried, and re-suspended in sterile STE buffer. RNA was removed by incubation with RNase (100 mg/ml; 5 Prime~3 Prime, Inc.) for 1 hour at 37° C., and the DNA re-extracted as described above. All procedures were performed in a sterile environment and all buffers and solutions were checked for the presence of LPS using the Pyrogent plus test. There was no detectable protein, viral RNA, or cellular DNA and less than 0.06 EU of endotoxin per mg of HSV DNA.

Mice

Female BALB/c (Harlan Sprague Dawley, Indianapolis, Ind.) were used for all experiments. Animals were housed and cared for as described elsewhere (Gangappa et al., *J Immunol.* 161:4289-4300, 1998).

Corneal Micropocket Assay

The murine corneal micropocket assay used in this work followed the general protocol of Kenyon et al., *Invest Ophthalmol Vis Sci*, 37:1625-1632, 1996. Pellets 0.4×0.4×0.2 mm$^3$ composed of sucralfate and hydron polymer were prepared (Kenyon et al., *Invest Ophthalmol Vis Sci*, 37: 625-1632, 1996). Known amounts of VEGF and DNA were added to these pellets prior to insertion into corneal pockets. The micropockets were placed 0.6-0.8 mm from the limbus (in the pericenter of the cornea at the lateral canthus of the eye) under stereomicroscopy (4 eyes/group). In some experiments, anti-mVEGF neutralizing antibody (5 µg in 5 µl of PBS) was injected subconjunctivally into the eyes of recipient mice just prior to and 2 days after pellet implantation.

Angiogenesis was quantitated at multiple times post pellet implantation under stereomicroscopy. Briefly, the length of the neovessels (in mm) generated from the limbal vessel ring toward the center of the cornea and the width of the neovessels presented in clock hours (each clock hour is equal to 30° C. at the circumference) was measured (Zheng et al., *Am J Pathol.* 159:1021-1029, 2001). The angiogenic area was calculated according to the formula for an ellipse. A=[(clock hours)×0.4×(vessel length in mm)×π]/2.

Immunohistochemical Staining

Eyes were removed and snap frozen in OCT compound (Miles Elkhart, Ind.). 6 µm sections were cut, air dried, and fixed in cold acetone for 10 minutes. The sections were blocked with 3% BSA and stained with biotinylated anti-mVEGF164. Sections were then treated with horseradish peroxidase-conjugated streptavidin (1:1000) and 3,3'-diaminobenzidine (Vector, Burlingame, Calif.) and counterstained with hematoxylin as previously described (Sparwasser et al., *Eur. J. Immunol.* 28:2045-2054, 1998). Cellular infiltration was determined microscopically by counting the infiltrating cells in the corneal stroma. Each data point represents the mean total cellular infiltrate in four central corneal sections from two eyes.

VEGF Staining of J774A.1 Cells

J774A.1 cells were plated and incubated in two-well chamber slides (Lab-Tek, Nalge Nunc International, Naperville, Ill.) or in 24-well plates (for later RT-PCR) in DMEM with 10% FBS overnight at 37° C. in 5% CO$_2$. The cells in chamber slides were co-cultured with FITC-labeled CpG ODN (1555) or control ODN (1471) at a concentration of 2 µg/10$^6$ cells. The cells were washed twice with PBS and fixed in a 1:1 mixture of acetone:methylalcohol at −20° C. for 15 minutes. The cells were stained with biotinylated rat-anti-mVEGF 6-18 hours post ODN stimulation and subsequently reacted with streptavidin-PE. Images were taken using a fluorescence microscope (Hamamatsu, Japan). The cells in 24-well plates were treated with 2 µg of ODN per 10$^6$ cells/ml. RNA from these cells was extracted for RT-PCR to detect VEGF MRNA (see RT-PCR methods section).

FA CS Staining of VEGF Expressing Cells

J774A.1 cells were treated with 0-8 µg/ml of ODN for 6-12 hours. The cells were then fixed in paraformaldehyde, blocked with FCS, and stained for VEGF using biotinylated rat-anti- mVEGF164 antibody followed by streptavidin-PE. Positive cells were identified by flow cytometry.

RNA Extraction and RT-PCR

10$^6$ J774A.1 cells were cultured with 2 µg of ODN for 3-6 hours. The cells were harvested in Tri-reagent (Molecular Biology Inc., Cincinnati, Ohio) and total RNA extracted as recommended by the manufacturer. Total RNA (10 µg) was reverse transcribed and aliquots of cDNA were used in a 25:1 PCR reaction as previously described (Takeshita et al., *Neuroreport.*, 12:3029-3032, 2001). The amplification profile was 94° C. for 1 minute, 65° C. for 1 minute, and 72° C. for 15 minutes for 30 cycles. The primer sequences for VEGF were:

5'-GCGGGCTGCCTCGCAGTC-3' (sense, SEQ ID NO: 10) and

5'-TCACCGCCTTGGCTTGTCAC-3' (antisense, SEQ ID NO: 11), respectively. RT-PCR products were 716 bp (mVEGF188), 644 bp (mVEGF164) and 512 bp (mVEGF120), respectively.

Statistical Analysis

Significant differences between groups were evaluated using the Student's t test. P≦0.05 was regarded as significant difference between two groups.

Example 2

Purified Herpes Simplex Virus DNA Stimulates Angiogenesis

HSV infection of mice can result in the blinding neovascular corneal lesions of stromal keratitis (SK) (1-3). To determine whether viral DNA plays a role in the pathogenesis of these lesions, DNA was purified from HSV infected cells. The HSV DNA was introduced into hydron pellets and surgically inserted into corneal micropockets established in the eyes of BALB/c mice. New blood vessel formation in the corneal limbus (emanating from the margin of the limbal vessel ring) was monitored daily. Initial experiments showed that HSV DNA elicited significant angiogenesis, as did pellets containing VEGF protein, but not those containing control herring sperm DNA (FIG. 1).

Dose response studies established that 90 ng of rhVEGF and 2 µg of HSV DNA triggered significant blood vessel formation (FIGS. 1 and 2). Angiogenesis developed within 24 hours of implantation, with the magnitude of new blood vessel formation progressing until the experiment was terminated on day 4. HSV DNA induced approximately half as much angiogenesis as did purified VEGF (FIG. 1), significantly exceeding the effect of empty hydron pellets or pellets containing control DNA (see FIG. 1).

Example 3

CpG DNA Induces Angiogenesis

The DNA sequence of HSV was analyzed to identify potentially pro-angiogenic motifs. Of interest, the frequency of bioactive CpG motifs present in the HSV genome was similar to that of bacterial DNA and was much higher than vertebrate DNA (Table 1).

TABLE 1

CpG expression frequency in HSV-1 versus murine DNA*

| Motif | Expression frequency | | | Fold difference |
| --- | --- | --- | --- | --- |
| | E. coli | Mouse | HSV-1 | |
| GACGTT | 1.3 | 0.11 | 0.82 | 7.5 |
| AGCGTT | 1.7 | 0.17 | 0.46 | 2.7 |
| AACGTC | 0.6 | 0.11 | 0.81 | 7.4 |

TABLE 1-continued

CpG expression frequency in HSV-1 versus murine DNA*

| Motif | Expression frequency | | | Fold difference |
|---|---|---|---|---|
| | E. coli | Mouse | HSV-1 | |
| AGCGTC | 1.3 | 0.15 | 0.95 | 6.3 |
| GGCGTC | 1.4 | 0.15 | 4.50 | 30.0 |
| GGCGTT | 2.5 | 0.15 | 1.68 | 11.2 |
| Average | 1.53 | 0.14 | 1.54 | 11.0 |

*The frequency with which each CpG hexamer is expressed in the genome of E. coli, mice and HSV-1 was determined using published sequence data (The mouse chromosome data was a composite of chromosomes 1-3. The GenBank accession numbers for mouse chromosome 1, 2 and 3 are: NT_025524, NT_019187 and NT_015485, respectively. The GenBank accession numbers for E. coli-K12 and for the HSV-1 complete genome are NC_000913 and X14112, respectively.). Note the significant over-expression of immunostimulatory GCGTC and GCGTT motifs in the HSV genome versus that of the mouse (fold difference).

To determine whether these CpG motifs (which are known to activate cells of the immune system and central nervous system) contribute to HSV-dependent angiogenesis, hydron pellets were infused with synthetic oligodeoxynucleotides (ODN) expressing CpG motifs. Pellets containing ≧1 ug of CpG ODN induced significant levels of angiogenesis (approximately 75% of that elicited by an optimal concentration of VEGF). The kinetics of new blood vessel formation induced by CpG ODN was indistinguishable from that of HSV DNA (FIG. 2). In contrast, the effect of control ODN (in which the CpG motif was eliminated by inversion) did not differ from empty hydron pellets (FIG. 2).

Example 4

Production of VEGF Characterizes CpG DNA Induced Angiogenesis

Based on previous evidence that HSV-associated angiogenesis involved the production of VEGF (Zheng et al., J Virol. 75:9828-9838, 2001) the ability of CpG DNA to stimulate VEGF secretion was evaluated. Histologic analysis of the region surrounding the corneal micropockets of animals treated with CpG DNA (both HSV DNA and CpG ODN) revealed that numerous inflammatory cells had infiltrated the site of pellet implantation (FIG. 3C, p≦0.01). These were primarily polymorphonuclear leukocytes and macrophages. Staining these sections with anti-VEGF Ab revealed that the infiltrating cells were producing VEGF protein (FIG. 3). Staining these sections with anti-VEGF antibody revealed that the infiltrating cells, and cells in the epithelium of eyes treated with CpG ODN, were producing VEFG protein (FIG. 3A). Significantly fewer VEGF expressing cells were present in the eyes of mice treated with control ODN or empty pellets (FIGS. 3A, 3B).

To determine whether the VEGF being produced by cells at the site of CpG DNA administration contributed to new blood vessel formation, neutralizing anti-VEGF antibody was administered subconjunctivally to these mice. As seen in FIG. 4, anti-VEGF Ab inhibited the angiogenesis induced by HSV DNA, CpG ODN and VEGF by approximately 70%. In contrast, anti-VEGF Ab had no effect on the background levels of angiogenesis observed using empty pellets or those containing control ODN.

Example 5

CpG DNA Stimulates VEGF Expression In Vitro

Figure 5:
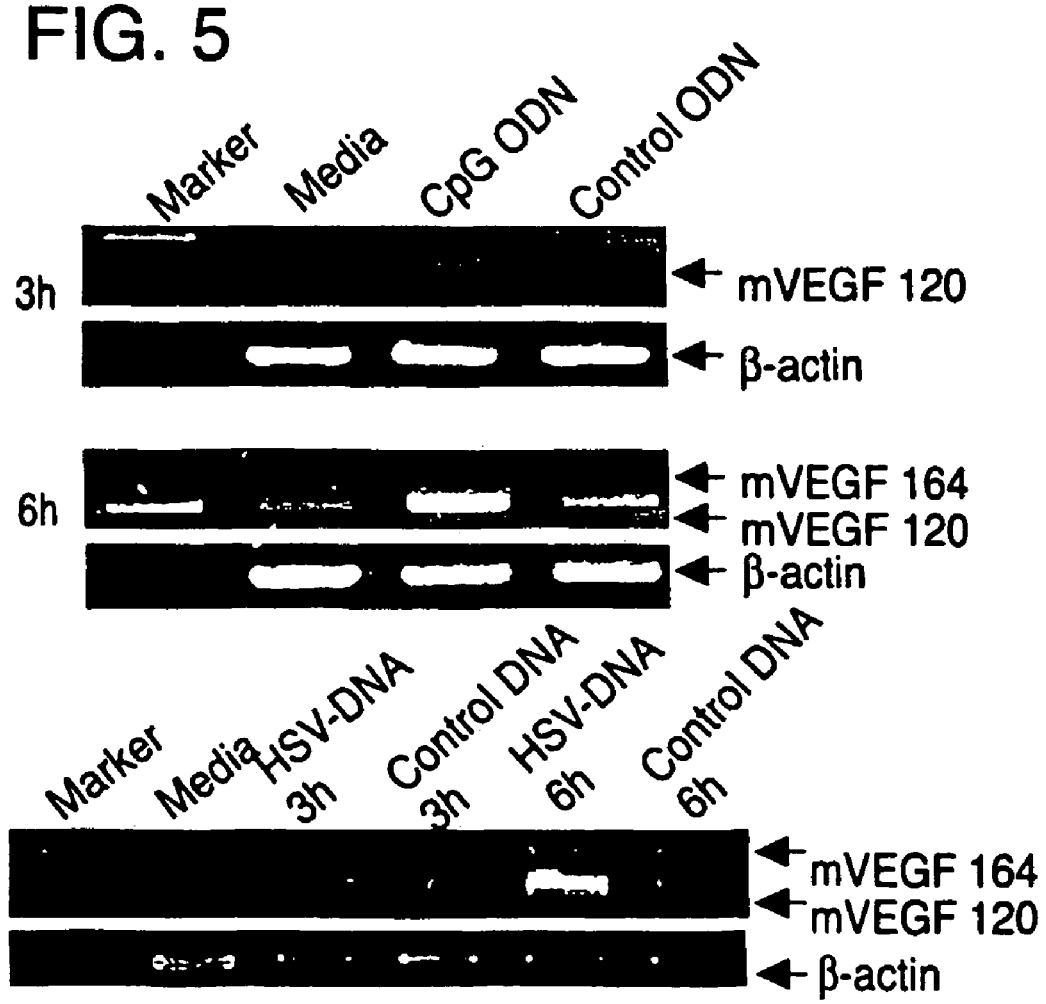
FIG. 5 is a digital image of a PCR analysis that demonstrates that CpG ODN upregulates VEGF mRNA expression in J774A.1 cells. J774A.1 cells were incubated for 3-6 hours with 3 µg/ml of HSV-DNA, herring sperm DNA, CpG or control ODN. Total RNA was extracted from $10^6$ cells, reverse transcribed and PCR amplified to detect the 120, 164, 188 isoforms of VEGF. β-actin served as the positive control and standard for semi-quantitative RT-PCR.

To verify that CpG DNA directly induced cells to produce VEGF, the J774A.1 murine macrophage cell line (which is known to produce VEGF when infected with HSV) was treated in vitro with 1-3 µg of HSV-DNA or herring sperm DNA, CpG or control ODN. As seen in FIG. 5, mRNA encoding the 120 isotype of VEGF was up-regulated within 3 hours of treatment with CpG but not control ODN. By 6 hours, expression of both the 120 and 164 isoforms of VEGF was induced by CpG ODN. In contrast, cells cultured in medium alone, or with control ODN, expressed minimal levels of VEGF mRNA.

A second series of experiments measured the production of VEGF protein by J774A.1 cells stimulated with CpG ODN. Fewer than 0.3% of untreated J774A.1 cells scored positive for VEGF protein (Table 2). The number of VEGF expressing cells increased within 6 hours of CpG ODN stimulation, with 20-26% of cells treated with 3 µg/ml CpG ODN producing protein at 24 hours (Table 2).

TABLE 2

Expression of VEGF following exposure of J774A.1 cells to CpG DNA

| Treatment | Dose (ug/ml) | % VEGF positive cells | |
|---|---|---|---|
| | | 6 h | 24 h |
| CpG ODN | 0.1 | 0.3 | 1.2 |
| | 1.0 | 9.1 | 21.7 |
| | 3.0 | 10.1 | 26.2 |
| | 8.0 | 12.6 | 15.3 |
| Control ODN | 3.0 | 4.5 | 5.3 |
| Media | | 0.1 | 0.3 |

J774A.1 cells were treated in vitro with 0.1-8.0 ug/ml of CpG ODN for 6 or 24 h. Cells expressing VEGF were identified by staining with rat-anti- mVEGF antibody (Ab). Results are representative of three independent experiments.

Figure 6:
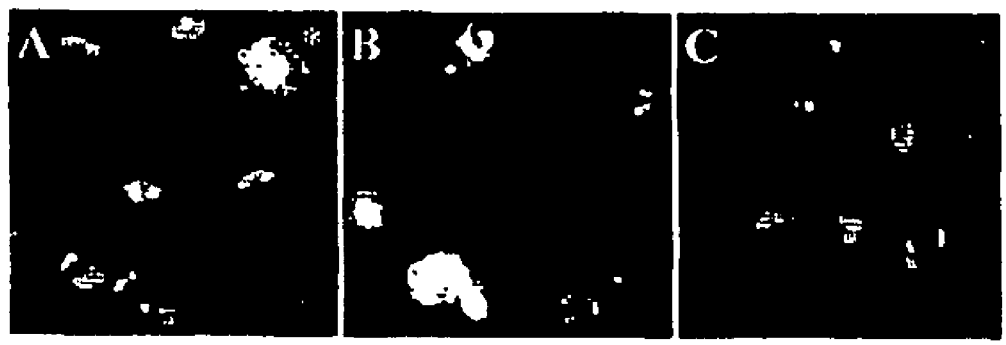
FIG. 6 is a set of digital images documenting that CpG ODN induces VEGF production. J774A.1 cells were incubated in two-well chamber slides with 2 µg/ml of FITC-CpG (FIGS. 6A and 6B) or control (FIG. 6C) ODN for 18 hours. The cells were fixed and stained for mVEGF at 18 hours (FIGS. 6B and 6C). Note that all cells expressing VEGF stained with FITC-CpG ODN. * An amplified photo image showed FITC-CpG ODN filled in the cytoplasm of a J774A.1 cell at 18 hours post stimulation. Magnification is 400.

This significantly exceeded the number of cells triggered to produce VEGF by control ODN. To determine whether VEGF production correlated with CpG ODN uptake, cultures were stimulated with fluorescein-labeled CpG ODN and simultaneously monitored for VEGF expression. All VEGF producing cells stained positive for CpG ODN, suggesting that CpG DNA directly triggered these cells to produce this angiogenic protein (FIG. 6).

Neovascularization anywhere along the visual axis poses a threat to ocular function. HSV infection of the eye is associated with new blood vessel formation in the normally avascular cornea (Zheng et al., J Virol., 75:9828-9835, 2001; Zheng et al., Am J Pathol, 159:1021-1029, 2001). The molecular mechanism(s) underlying this effect are poorly defined, although evidence suggests that VEGF (a highly potent pro-angiogenic host protein (Ferrara, Nature, 380:439-442, 1996; Ferrara, Curr. Top. Microbio. Immunol., 327:1-30, 1999; Yancopoulos, Nature, 407:242-248, 2000) is involved, at least indirectly (Zheng et al., J Virol., 75:9828-9835, 2001). The work disclosed herein provides evidence that HSV DNA, likely through its content of bioactive CpG motifs, contributes to virus-induced ocular angiogenesis. Without being bound by theory, these findings provide a mechanism by which HSV infection induces angiogenesis during herpetic stromal keratitis.

CpG ODN express a wide range of biological activities. They are potent vaccine adjuvants, anti-allergens, and trigger an protective innate immune response (Klinman, *Antisense Nucleic Acid Drug Dev.,* 8:181-184, 1998; Davis et al., *J Immunol,* 160:870-876, 1998; Broide et al., *J Immunol,* 161: 7054-7062, 1998; Krieg et al., *J Immunol,* 161:2428-2434, 1998). Several recent reports indicate that CpG ODN also stimulate cells of the central nervous system (Takeshita et al., *Neuroreport,* 12:3029-3032, 2001). Although CpG ODN have many potential uses, their potential to induce angiogenesis has not been previously recognized. The experiments disclosed herein document that bioactive CpG motifs induce dose-dependent neovascularization in the corneas of mice engrafted with hydron pellets containing CpG ODN or HSV DNA. The degree of angiogenesis elicited by an optimal amount of CpG ODN was approximately 75% of that induced by the potent angiogenic factor VEGF. This activity was motif specific, since ODN in which the critical CpG dinucleotide was inverted to a GpC lacked function.

Without being bound by theory, the results suggest that, rather than triggering new blood vessel formation directly, CpG motifs stimulate host cells to secrete VEGF, which in turn induces neovascularization. Several findings are consistent with this model. First, CpG ODN were taken up by the same inflammatory cells that expressed VEGF. Second, exposure to CpG motifs directly stimulated J774A.1 murine macrophages to produce VEGF. Finally, local administration of anti-VEGF antibodies to CpG DNA treated eyes significantly inhibited corneal angiogenesis.

These studies were undertaken to elucidate the mechanism by which ocular infection with HSV causes angiogenesis, an essential event in the pathogenesis of herpetic stromal keratitis (Zheng et al., *J Virol.,* 75:9828-9835, 2001; Zheng et al., *Am J Pathol,* 159:1021-1029, 2001). The HSV genome has a codon usage that favors C and G (Roizman, *Cell* 16:481-494, 1979). In consequence the HSV genome contains a significantly higher frequency of bioactive CpG motifs than does vertebrate DNA (Table 1). This pattern of CpG expression is reminiscent of bacterial DNA, which has well-established pro-inflammatory effects (Krieg et al., *Nature,* 374:546-549, 1995; Klimnan et al., *Proc Natl Acad Sci USA,* 93:2879-2883, 1996). The results disclosed herein expand the list of activities mediated by CpG DNA to include angiogetiesis and the induction of VEGF secretion.

Example 6

Animal Model for Identifying Agents that Inhibit Angiogenesis

Neovascular diseases are a serious problem in the eye. For example, in retinal diseases such as diabetic retinopathy and macular degeneration, inappropriate vascularization of the retina is part of the pathogenic process that can lead to blindness. In addition, neovascularization of the cornea is a serious problem in chronic inflammatory conditions of the eye, such as Herpes Simplex infection and corneal transplant rejection. Clearly, there is a need to identify agents that inhibit in appropriate pathological neovascularization in the eye.

Thus, in one embodiment, an animal model of neovascularization in the eye is provided. In this model system CpG ODN are administered to an area of the eye to induce neovascularization. Potential therapeutic agents of interest are administered to the animal model in order to identify agents that inhibit vascularization, or reverse existing neovascularization. Specific, non-limiting examples of agents of interest include photodynamic therapy agents (see U. S. Pat. No. 6,225,303) and steroids (e.g. see U.S. Pat. No. 5,929,111), amongst others (see published PCT Application No. WO 90/04409A). In one embodiment, induced neovascularization in an animal to which the potentially therapeutic agent has been administered is compared with a control animal to which the potentially therapeutic agent has not been administered.

In one embodiment, a corneal micropocket assay is utilized (see Example 1 and Kenyon et al., *Invest Ophthalmol Vis Sci,* 37:1625-1632, 1996. Pellets 0.4×0.4×0.2 mm$^3$ are composed of sucralfate and hydron polymer are prepared (Sparwasser et al., *Eur. J Immunol* 27:1671-1679, 1997). Known amounts of DNA are added to these pellets prior to insertion into corneal pockets. The micropockets are placed 0.6-0.8 mm from the limbus (in the pericenter of the cornea at the lateral canthus of the eye) under stereomicroscopy (4 eyes/group). One group of animals is transplanted with pellets including CpG ODN, and is treated with an agent of interest, while a second group of animals is transplanted with pellets including CpG ODN, but are not treated with the agent of interest. The agent of interest can be administered at the time of transplantation, or can be administered subsequent to transplantation.

Angiogenesis is quantitated at multiple times post pellet implantation under stereomicroscopy. Briefly, the length of the neovessels (in mm) generated from the limbal vessel ring toward the center of the cornea and the width of the neovessels presented in clock hours (each clock hour is equal to 30° C. at the circumference) is measured (Zheng et al., *J Virol,* 75:9828-9835, 2001), and the angiogenic area is calculated as described in Example 1. The angiogenic area of the animals treated with the agent of interest is then compared to the angiogenic area of the control animals. An agent is identified as being of interest (e.g. "anti-angiogenic") if the angiogenic area is decreased by at least 25%, at least 50%, at least 75:, or at least 90%.

Example 7

ODN Sequences

Exemplary K ODN, D ODN, K ODN control, and D ODN control sequences are listed below in Table 1.

TABLE 3

| ODN | SEQUENCE | SEQUENCE IDENTIFIER |
|---|---|---|
| D ODN | | |
| DV104 | GGTGCATCGATGCAGGGGGG | (SEQ ID NO: 12) |
| DV19 | GGTGCATCGATGCAGGGGGG | (SEQ ID NO: 12) |
| DV29 | GGTGCACCGGTGCAGGGGGG | (SEQ ID NO: 13) |
| DV35 | GGTGCATCGATGCAGGGGGG | (SEQ ID NO: 12) |
| DV28 | GGTGCGTCGATGCAGGGGGG | (SEQ ID NO: 14) |
| DV106 | GGTGTGTCGATGCAGGGGGG | (SEQ ID NO: 15) |
| DV116 | TGCATCGATGCAGGGGGG | (SEQ ID NO: 16) |
| DV113 | GGTGCATCGATACAGGGGGG | (SEQ ID NO: 17) |
| DV34 | GGTGCATCGATGCAGGGGGG | (SEQ ID NO: 12) |
| DV102 | GGTGCATCGTTGCAGGGGGG | (SEQ ID NO: 18) |
| DV32 | GGTGCGTCGACGCAGGGGGG | (SEQ ID NO: 19) |
| DV117 | GGTCGATCGATGCACGGGGG | (SEQ ID NO: 20) |
| DV37 | GGTGCATCGATGCAGGGGGG | (SEQ ID NO: 12) |
| DV25 | GGTGCATCGATGCAGGGGGG | (SEQ ID NO: 12) |
| DV30 | GGTGCATCGACGCAGGGGGG | (SEQ ID NO: 21) |
| dv120 | GGTGCATCGATAGGCGGGGG | (SEQ ID NO: 22) |
| DV27 | GGTGCACCGATGCAGGGGGG | (SEQ ID NO: 23) |
| dv119 | CCTGCATCGATGCAGGGGGG | (SEQ ID NO: 24) |
| D142 | GGTATATCGATATAGGGGGG | (SEQ ID NO: 25) |
| d143 | GGTGGATCGATCCAGGGGGG | (SEQ ID NO: 26) |

TABLE 3-continued

| ODN | SEQUENCE | SEQUENCE IDENTIFIER |
|---|---|---|
| D CONTROLS | | |
| dv17 | GGTGCAACGTTGCAGGGGGG | (SEQ ID NO: 27) |
| DV78 | GGTGCATCGATAGAGGGGGG | (SEQ ID NO: 28) |
| DV96 | GGTGCATCGTAGCAGGGGGG | (SEQ ID NO: 29) |
| DV95 | GGTGGTTCGATGCAGGGGGG | (SEQ ID NO: 30) |
| DV93 | GGTGCATCGATGCAGGGGGG | (SEQ ID NO: 12) |
| DV92 | GGTGCACCGGTGCAAAAAAA | (SEQ ID NO: 31) |
| DV81 | GGTGCATCGATAGAGGGG | (SEQ ID NO: 32) |
| DV77 | GGTGCATCGATGCAGGGGGG | (SEQ ID NO: 12) |
| DV76 | GGTGCATCGATGCAAAAAAA | (SEQ ID NO: 33) |
| DV71 | GGGGTCGACAGGG | (SEQ ID NO: 34) |
| DV49 | GGTGCATAAATGCAGGGGGG | (SEQ ID NO: 35) |
| DV48 | GGTGCATCAATGCAGGGGGG | (SEQ ID NO: 36) |
| DV47 | GGTGCATTGATGCAGGGGGG | (SEQ ID NO: 37) |
| DV45 | GGTGCATC*GATGCAGGGGGG | (SEQ ID NO: 38) |
| DV26 | GGTGCATGCATGCAGGGGGG | (SEQ ID NO: 39) |
| DV20 | GGTGCATGCATGCAGGGGGG | (SEQ ID NO: 39) |
| DV122 | GGTGCATTGATGCAGGGGGG | (SEQ ID NO: 37) |
| DV114 | GGTGCACTGGTGCAGGGGGG | (SEQ ID NO: 40) |
| DV111 | GGTGTATCGATGCAAAAGGG | (SEQ ID NO: 41) |
| DV108 | GGTGCCCCGTTGCAGGGGGG | (SEQ ID NO: 42) |
| DV107 | GGTGCAACGGGGCAGGGGGG | (SEQ ID NO: 43) |
| DV105 | AATGCATCGATGCAAAAAAA | (SEQ ID NO: 44) |
| DV103 | GGTGCACCGTGGCAGGGGGG | (SEQ ID NO: 45) |
| DV100 | GGTGCATCGAAGCAGGGGGG | (SEQ ID NO: 46) |
| d79 | GGTGGATCGATGCAGGGGGG | (SEQ ID NO: 47) |
| d145 | GGTGCACGCGTGCAGGGGGG | (SEQ ID NO: 48) |
| d144 | GGTGCATGTATGCAGGGGGG | (SEQ ID NO: 49) |
| AA20 | GGGGGATCGATGGGGG | (SEQ ID NO: 50) |
| AA3M | GGGGGAAGCTTCGGGG | (SEQ ID NO: 51) |
| K ODN | | |
| K22 | CTCGAGCGTTCTC | (SEQ ID NO: 52) |
| DV84 | ACTCTCGAGCGTTCTA | (SEQ ID NO: 53) |
| K21 | TCTCGAGCGTTCTC | (SEQ ID NO: 54) |
| K82 | ACTCTGGAGCGTTCTC | (SEQ ID NO: 55) |
| K30 | TGCAGCGTTCTC | (SEQ ID NO: 56) |
| k31 | TCGAGGCTTCTC | (SEQ ID NO: 57) |
| K39 | GTCGGCGTTGAC | (SEQ ID NO: 58) |
| K16 | TCGACTCTCGAGCGTTCTC | (SEQ ID NO: 59) |
| K3 | ATCGACTCTCGAGCGTTCTC | (SEQ ID NO: 60) |
| k23 | TCGAGCGTTCTC | (SEQ ID NO: 61) |
| DV110 | TCGAGGCTTCTC | (SEQ ID NO: 57) |
| K40 | GTCGGCGTCGAC | (SEQ ID NO: 62) |
| DV101 | CTCGAGCGTTCT | (SEQ ID NO: 63) |
| DV89 | ACTCTTTCGTTCTC | (SEQ ID NO: 64) |
| K34 | GTCGACGTTGAC | (SEQ ID NO: 65) |
| DV86 | ACTCTCGAGCGTTCTC | (SEQ ID NO: 66) |
| K83 | ACTCTCGAGGGTTCTC | (SEQ ID NO: 67) |
| K19 | ACTCTCGAGCGTTCTC | (SEQ ID NO: 66) |
| DV88 | ACTCTCGAGCGTTCTCAAAA | (SEQ ID NO: 68) |
| DV85 | CATCTCGAGCGTTCTC | (SEQ ID NO: 69) |
| K73 | GTCGTCGATGAC | (SEQ ID NO: 70) |
| DV109 | TCGAGCGTTCT | (SEQ ID NO: 71) |
| D123 | TCGTTCGTTCTC | (SEQ ID NO: 72) |
| D124 | TCGTTTGTTCTC | (SEQ ID NO: 73) |
| K46 | GTCGACGCTGAC | (SEQ ID NO: 74) |
| D139 | TCGATGCTTCTC | (SEQ ID NO: 75) |
| D137 | TCGCCGCTTCTC | (SEQ ID NO: 76) |
| K47 | GTCGACGTCGAC | (SEQ ID NO: 38) |
| K72 | GTCATCGATGCA | (SEQ ID NO: 77) |
| DV90 | ACTCTTTCGATCTC | (SEQ ID NO: 78) |
| K37 | GTCAGCGTCGAC | (SEQ ID NO: 79) |
| k25 | TCGAGCGTTCT | (SEQ ID NO: 71) |
| D127 | TGGAGCGTTCTC | (SEQ ID NO: 80) |
| D138 | TGCTGCGTTCTC | (SEQ ID NO: 81) |
| D125 | TTGAGCGTACTC | (SEQ ID NO: 82) |
| D134 | TGCTTCGAGCTC | (SEQ ID NO: 83) |
| D136 | TGCACCGTTCTC | (SEQ ID NO: 84) |
| CONTROL K ODN | | |
| DV89 | ACTCTTTCGTTCTC | (SEQ ID NO: 64) |
| d112 | TGCAGGCTTCTC | (SEQ ID NO: 85) |
| DV112 | TTGAGTGTTCTC | (SEQ ID NO: 86) |
| DV112 | TTGAGTGTTCTC | (SEQ ID NO: 86) |
| K41 | GTCGGCGCTGAC | (SEQ ID NO: 87) |
| DV109 | TCGAGCGTTCT | (SEQ ID NO: 71) |
| k10 | ATGCACTCTGCAGGCTTCTC | (SEQ ID NO: 88) |
| K38 | GTCAGCGCTGAC | (SEQ ID NO: 89) |
| k29 | TCGAGCG | (SEQ ID NO: 90) |
| k26 | TCGAGCGTTC | (SEQ ID NO: 91) |
| k27 | TCGAGCGTT | (SEQ ID NO: 92) |
| K36 | GTCAACGCTGAC | (SEQ ID NO: 93) |
| K35 | GTCAACGTCGAC | (SEQ ID NO: 94) |
| K44 | GTCGAGGCCGAC | (SEQ ID NO: 95) |
| k28 | TCGAGCGT | (SEQ ID NO: 96) |
| AA19 | GGGGGAACGTTGGGGG | (SEQ ID NO: 97) |
| D135 | TGCAGCGAGCTC | (SEQ ID NO: 98) |
| D141 | CCGAGGCTTCTC | (SEQ ID NO: 99) |
| D126 | ACGAGGGTTCTC | (SEQ ID NO: 100) |
| K42 | GTCAACGCCGAG | (SEQ ID NO: 101) |
| D140 | GCGAGGCTTCTC | (SEQ ID NO: 102) |
| d121 | ACTCTTGAGTGTTCTC | (SEQ ID NO: 103) |
| K45 | GTCGGCGCCGAC | (SEQ ID NO: 104) |
| K43 | GTCAGCGCCGAC | (SEQ ID NO: 105) |
| K24 | CGAGCGTTCTC | (SEQ ID NO: 106) |

Underlined bases are phosphodiester.
*indicates methylated CG.
Bold indicates self-complementary sequences. Sequence identifier is noted below the nucleic acid sequence. For each heading (IFN-g, IL-6, IgM, PRO-LIF (proliferation)) first column is average and second column is standard deviation.

This disclosure provides methods for stimulating angiogenesis using CpG ODN. The disclosure further provides methods for inducing the production of VEFG using CpG ODN. In addition, an model system for screening potential anti-angiogenic agents is provided. It will be apparent that the precise details of the methods described may be varied or modified without departing from the spirit of the described invention. We claim all such modifications and variations that fall within the scope and spirit of the claims below.

The invention claimed is:

1. A method of inducing neovascularization in a tissue, comprising introducing a CpG oligodeoxynucleotide into an area of the tissue wherein the formation of new blood vessels is desired, wherein the CpG oligodeoxynucleotide has a sequence as set forth as:

5'-N$_1$DCGYN$_2$-3'     (SEQ ID NO: 2)

wherein at least one nucleotide separates consecutive CpGs; D is adenine, guanine, or thymidine; Y is cytosine or thymine, N is any nucleotide and N$_1$+N$_2$ is from 0-26 bases; or

5'-N$_1$RDCGYTN$_2$-3'     (SEQ ID NO: 4)

wherein at least one nucleotide separates consecutive CpGs; RD is selected from the group consisting of GpT, GpG, GpA, ApT and ApA; YT is selected from the group consisting of TpT or CpT; N is any nucleotide and N$_1$+N$_2$ is from 0-26 bases; and wherein the CpG oligodeoxynucleotide is 8 to 30 nucleotides in length, thereby inducing neovascularization in the area of the tissue, wherein the tissue is a skin graft.

2. A method of inducing neovascularization in a tissue, comprising introducing a CpG oligodeoxynucleotide into an area of the tissue wherein the formation of new blood vessels is desired, wherein the CpG oligodeoxynucleotide has a sequence as set forth as:

5'-N$_1$DCGYN$_2$-3'     (SEQ ID NO: 2)

wherein at least one nucleotide separates consecutive CpGs; D is adenine, guanine, or thymidine; Y is cytosine or thymine, N is any nucleotide and N$_1$+N$_2$ is from 0-26 bases; or

5'-N$_1$RDCGYTN$_2$-3'     (SEQ ID NO:4)

wherein at least one nucleotide separates consecutive CpGs; RD is selected from the group consisting of GpT, GpG, GpA, ApT and ApA; YT is selected from the group consisting of TpT or CpT; N is any nucleotide and N$_1$+N$_2$ is from 0-26 bases; and wherein the CpG oligodeoxynucleotide is 8 to 30 nucleotides in length, thereby inducing neovascularization in the area of the tissue, wherein the tissue is the scalp.

3. A method of inducing neovascularization in a tissue, comprising introducing a CpG oligodeoxynucleotide into an area of the tissue wherein the formation of new blood vessels is desired, wherein the CpG oligodeoxynucleotide has a sequence as set forth as:

5'-N$_1$DCGYN$_2$-3'     (SEQ ID NO: 2)

wherein at least one nucleotide separates consecutive CpGs; D is adenine, guanine, or thymidine; Y is cytosine or thymidine, N is any nucleotide and N$_1$+N$_2$ is from 0-26 bases; or

5'-N$_1$RDCGYTN$_2$-3'     (SEQ ID NO: 4)

wherein at least one nucleotide separates consecutive CpGs; RD is selected from the group consisting of GpT, GpG, GpA, ApT and ApA; YT is selected from the group consisting of TpT or CpT; N is any nucleotide and N$_1$+N$_2$ is from 0-26 bases; and wherein the CpG oligodeoxynucleotide is 8 to 30 nucleotides in length, thereby inducing neovascularization in the area of the tissue, wherein the tissue comprises a blood vessel.

4. The method of claim 1, wherein the CpG oligodeoxynucleotide comprises the nucleic acid sequence set forth as SEQ ID NO: 8.

5. A method of promoting angiogenesis in an area of a subject where angiogenesis is desired, comprising introducing a CpG oligodeoxynucleotide to the area, wherein the CpG oligodeoxynucleotide has a sequence as set forth as:

5'-N$_1$DCGYN$_2$-3'     (SEQ ID NO: 2)

wherein at least one nucleotide separates consecutive CpGs; D is adenine, guanine, or thymidine; Y is cytosine or thymidine, N is any nucleotide and $N_1+N_2$ is from 0-26 bases; or

```
5'-N₁RDCGYTN₂-3'        (SEQ ID NO: 4)
``` wherein at least one nucleotide separates consecutive CpGs; RD is selected from the group consisting of GpT, GpG, GpA, ApT and ApA; YT is selected from the group consisting of TpT or CpT; N is any nucleotide and $N_1+N_2$ is from 0-26 bases; and wherein the CpG oligodeoxynucleotide is 8 to 30 nucleotides in length thereby promoting angiogenesis in the subject, wherein the subject has peripheral vascular disease, and wherein the area is a vessel in which blood flow is restricted.

6. The method of claim 1, wherein the oligodeoxynucleotide comprises the nucleic acid sequence set forth as SEQ ID NO: 7.

7. The method of claim 2, wherein the oligodeoxynucleotide comprises the nucleic acid sequence set forth as SEQ ID NO: 7.

8. The method of claim 3, wherein the oligodeoxynucleotide comprises the nucleic acid sequence set forth as SEQ ID NO: 7.

9. The method of claim 1, wherein the oligodeoxynucleotide consists of the nucleic acid sequence set forth as SEQ ID NO: 7.

10. The method of claim 2, wherein the oligodeoxynucleotide consists of the nucleic acid sequence set forth as SEQ ID NO: 7.

11. The method of claim 3, wherein the oligodeoxynucleotide consists of the nucleic acid sequence set forth as SEQ ID NO: 7.

12. The method of claim 2, wherein the CpG oligodeoxynucleotide comprises the nucleic acid sequence as set forth as SEQ ID NO: 8.

13. The method of claim 3, wherein the CpG oligodeoxynucleotide comprises the nucleic acid sequence as set forth as SEQ ID NO: 8.

14. The method of claim 5, wherein the CpG oligodeoxynucleotide comprises the nucleic acid sequence as set forth as SEQ ID NO: 7.

15. The method of claim 5, wherein the CpG oligodeoxynucleotide consists of the nucleic acid sequence as set forth as SEQ ID NO: 8.

16. The method of claim 1, wherein the CpG oligodeoxynucleotide comprises one of the nucleic acid sequence set forth as SEQ ID NO: 38, SEQ ID NO: 52, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 65, SEQ ID NO: 66, SEQ ID NO: 67, SEQ ID NO: 70, SEQ ID NO: 71, SEQ ID NO: 74, SEQ ID NO: 77, or SEQ ID NO: 79.

17. The method of claim 2, wherein the CpG oligodeoxynucleotide comprises one of the nucleic acid sequence set forth as SEQ ID NO: 38, SEQ ID NO: 52, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 65, SEQ ID NO: 66, SEQ ID NO: 67, SEQ ID NO: 70, SEQ ID NO: 71, SEQ ID NO: 74, SEQ ID NO: 77, or SEQ ID NO: 79.

18. The method of claim 3, wherein the CpG oligodeoxynucleotide comprises one of the nucleic acid sequence set forth as SEQ ID NO: 38, SEQ ID NO: 52, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 65, SEQ ID NO: 66, SEQ ID NO: 67, SEQ ID NO: 70, SEQ ID NO: 71, SEQ ID NO: 74, SEQ ID NO: 77, or SEQ ID NO: 79.

19. The method of claim 5, wherein the CpG oligodeoxynucleotide comprises one of the nucleic acid sequence set forth as SEQ ID NO: 38, SEQ ID NO: 52, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 65, SEQ ID NO: 66, SEQ ID NO: 67, SEQ ID NO: 70, SEQ ID NO: 71, SEQ ID NO: 74, SEQ ID NO: 77, or SEQ ID NO: 79.

* * * * *

UNITED STATES PATENT AND TRADEMARK OFFICE
CERTIFICATE OF CORRECTION

PATENT NO. : 7,615,227 B2　　　　　　　　　　　　　　　　　　Page 1 of 1
APPLICATION NO. : 10/499597
DATED : November 10, 2009
INVENTOR(S) : Klinman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1306 days.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,615,227 B2  
APPLICATION NO. : 10/499597  
DATED : November 10, 2009  
INVENTOR(S) : Klinman et al.

Page 1 of 1

It is certified that error appears in the above-identified patent and that said Letters Patent is hereby corrected as shown below:

On the Title Page, Item (73) Assignees:

Page 1, left column, at Assignees: "The United States of America as represented by the Secretary of the Department of Health and Human Services, Washington, DC," should read --The United States of America as represented by the Secretary of the Department of Health and Human Services, Washington, DC (US); University of Tennessee Research Foundation, Knoxville, TN (US)--.

Signed and Sealed this  
Twenty-fourth Day of September, 2013

Teresa Stanek Rea  
*Deputy Director of the United States Patent and Trademark Office*

SEQUENCE LISTING

<160> NUMBER OF SEQ ID NOS: 106

<210> SEQ ID NO 1
<211> LENGTH: 10
<212> TYPE: DNA
<213> ORGANISM: Artificial Sequence
<220> FEATURE:
<223> OTHER INFORMATION: CpG K oligonucleotide

```
<220> FEATURE:
<221> NAME/KEY: misc_feature
<222> LOCATION: (1)..(10)
<223> OTHER INFORMATION: n equals any nucleotide

<400> SEQUENCE: 1 nnndcgwnnn                                                            10

<210> SEQ ID NO 2
<211> LENGTH: 6
<212> TYPE: DNA
<213> ORGANISM: Artificial Sequence
<220> FEATURE:
<223> OTHER INFORMATION: CpG K oligonucleotide
<220> FEATURE:
<221> NAME/KEY: misc_feature
<222> LOCATION: (1)..(6)
<223> OTHER INFORMATION: n equals any nucleotide

<400> SEQUENCE: 2 ndcgyn                                                                 6

<210> SEQ ID NO 3
<211> LENGTH: 20
<212> TYPE: DNA
<213> ORGANISM: Artificial Sequence
<220> FEATURE:
<223> OTHER INFORMATION: CpG K oligonucleotide

<400> SEQUENCE: 3
ataatcgacg ttcaagcaag                                                 20

<210> SEQ ID NO 4
<211> LENGTH: 8
<212> TYPE: DNA
<213> ORGANISM: Artificial Sequence
<220> FEATURE:
<223> OTHER INFORMATION: CpG K oligonucleotide
<220> FEATURE:
<221> NAME/KEY: misc_feature
<222> LOCATION: (1)..(8)
<223> OTHER INFORMATION: n equals any nucleotide

<400> SEQUENCE: 4 nrdcgytn                                                               8

<210> SEQ ID NO 5
<211> LENGTH: 11
<212> TYPE: DNA
<213> ORGANISM: Artificial Sequence
<220> FEATURE:
<223> OTHER INFORMATION: CpG D oligonucleotide
<220> FEATURE:
<221> NAME/KEY: misc_feature
<222> LOCATION: (1)..(10)
<223> OTHER INFORMATION: n equals any nucleotide

<400> SEQUENCE: 5
nnntcgwnnn y                                                          11

<210> SEQ ID NO 6
<211> LENGTH: 14
<212> TYPE: DNA
<213> ORGANISM: Artificial Sequence
<220> FEATURE:
<223> OTHER INFORMATION: CpG D oligonucleotide
<220> FEATURE:
<221> NAME/KEY: misc_feature
<222> LOCATION: (1)..(13)
```

```
<223> OTHER INFORMATION: n equals any nucleotide

<400> SEQUENCE: 6
nnnrycgryn nnng                                                    14

<210> SEQ ID NO 7
<211> LENGTH: 10
<212> TYPE: DNA
<213> ORGANISM: Artificial Sequence
<220> FEATURE:
<223> OTHER INFORMATION: Exemplary angiogenic CpG oligonucleotide

<400> SEQUENCE: 7
tcaacgttga                                                         10

<210> SEQ ID NO 8
<211> LENGTH: 15
<212> TYPE: DNA
<213> ORGANISM: Artificial Sequence
<220> FEATURE:
<223> OTHER INFORMATION: Exemplary angiogenic CpG oligonucleotide

<400> SEQUENCE: 8
gctagacgtt agcgt                                                   15

<210> SEQ ID NO 9
<211> LENGTH: 10
<212> TYPE: DNA
<213> ORGANISM: Artificial Sequence
<220> FEATURE:
<223> OTHER INFORMATION: Exemplary control CpG oligonucleotide

<400> SEQUENCE: 9
tcaagcttga                                                         10

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 10
gcgggctgcc tcgcagtc                                                18

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
tcaccgcctt ggcttgtcac                                              20

<210> SEQ ID NO 12
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 12
ggtgcatcga tgcaggggg                                               20
```

```
<210> SEQ ID NO 13
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 13
ggtgcaccgg tgcagggggg                                               20

<210> SEQ ID NO 14
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 14
ggtgcgtcga tgcagggggg                                               20

<210> SEQ ID NO 15
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 15
ggtgtgtcga tgcagggggg                                               20

<210> SEQ ID NO 16
<211> LENGTH: 18
<212> TYPE: DNA
<213> ORGANISM: Artificial Sequence
<220> FEATURE:
<223> OTHER INFORMATION: CpG D oligonucleotide

<400> SEQUENCE: 16
tgcatcgatg cagggggg                                                 18

<210> SEQ ID NO 17
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 17
ggtgcatcga tacagggggg                                               20

<210> SEQ ID NO 18
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 18
ggtgcatcgt tgcagggggg                                               20

<210> SEQ ID NO 19
<211> LENGTH: 20
<212> TYPE: DNA
<213> ORGANISM: Artificial Sequence
<220> FEATURE:
<223> OTHER INFORMATION: CpG D oligonucleotide
```

```
<400> SEQUENCE: 19
ggtgcgtcga cgcaggggggg                                              20

<210> SEQ ID NO 20
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 20
ggtcgatcga tgcacgggggg                                              20

<210> SEQ ID NO 21
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 21
ggtgcatcga cgcaggggggg                                              20

<210> SEQ ID NO 22
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 22
ggtgcatcga taggcggggg                                               20

<210> SEQ ID NO 23
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 23
ggtgcaccga tgcaggggggg                                              20

<210> SEQ ID NO 24
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 24
cctgcatcga tgcaggggggg                                              20

<210> SEQ ID NO 25
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 25
ggtatatcga tataggggggg                                              20

<210> SEQ ID NO 26
<211> LENGTH: 20
```

```
<212> TYPE: DNA
<213> ORGANISM: Artificial Sequence
<220> FEATURE:
<223> OTHER INFORMATION: CpG D oligonucleotide

<400> SEQUENCE: 26
ggtggatcga tccaggggggg                                                      20

<210> SEQ ID NO 27
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 27
ggtgcaacgt tgcaggggggg                                                      20

<210> SEQ ID NO 28
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 28
ggtgcatcga tagaggggggg                                                      20

<210> SEQ ID NO 29
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 29
ggtgcatcgt agcaggggggg                                                      20

<210> SEQ ID NO 30
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 30
ggtggttcga tgcaggggggg                                                      20

<210> SEQ ID NO 31
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 31
ggtgcaccgg tgcaaaaaaa                                                       20

<210> SEQ ID NO 32
<211> LENGTH: 18
<212> TYPE: DNA
<213> ORGANISM: Artificial Sequence
<220> FEATURE:
<223> OTHER INFORMATION: CpG D oligonucleotide

<400> SEQUENCE: 32
```
ggtgcatcga tagagggg                      18

<210> SEQ ID NO 33
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 33
ggtgcatcga tgcaaaaaaa                    20

<210> SEQ ID NO 34
<211> LENGTH: 13
<212> TYPE: DNA
<213> ORGANISM: Artificial Sequence
<220> FEATURE:
<223> OTHER INFORMATION: CpG D oligonucleotide

<400> SEQUENCE: 34
ggggtcgaca ggg                           13

<210> SEQ ID NO 35
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 35
ggtgcataaa tgcagggggg                    20

<210> SEQ ID NO 36
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 36
ggtgcatcaa tgcagggggg                    20

<210> SEQ ID NO 37
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 37
ggtgcattga tgcagggggg                    20

<210> SEQ ID NO 38
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 38
ggtgcatcga tgcagggggg                    20

<210> SEQ ID NO 39
<211> LENGTH: 20
<212> TYPE: DNA
<213> ORGANISM: Artificial Sequence

```
<220> FEATURE:
<223> OTHER INFORMATION: CpG D oligonucleotide

<400> SEQUENCE: 39
ggtgcatgca tgcagggggg                                              20

<210> SEQ ID NO 40
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 40
ggtgcactgg tgcaggggg                                               20

<210> SEQ ID NO 41
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 41
ggtgtatcga tgcaaaaggg                                              20

<210> SEQ ID NO 42
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 42
ggtgccccgt tgcaggggg                                               20

<210> SEQ ID NO 43
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 43
ggtgcaacgg ggcaggggg                                               20

<210> SEQ ID NO 44
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 44
aatgcatcga tgcaaaaaaa                                              20

<210> SEQ ID NO 45
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 45
ggtgcaccgt ggcaggggg                                               20
```

<210> SEQ ID NO 46
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 46
ggtgcatcga agcaggggg                                              20

<210> SEQ ID NO 47
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 47
ggtggatcga tgcaggggg                                              20

<210> SEQ ID NO 48
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 48
ggtgcacgcg tgcaggggg                                              20

<210> SEQ ID NO 49
<211> LENGTH: 20
<212> TYPE: DNA
<213> ORGANISM: Artificial Sequence
<220> FEATURE:
<223> OTHER INFORMATION: CpG D oligonucleotide

<400> SEQUENCE: 49
ggtgcatgta tgcaggggg                                              20

<210> SEQ ID NO 50
<211> LENGTH: 16
<212> TYPE: DNA
<213> ORGANISM: Artificial Sequence
<220> FEATURE:
<223> OTHER INFORMATION: CpG D oligonucleotide

<400> SEQUENCE: 50
gggggatcga tggggg                                                 16

<210> SEQ ID NO 51
<211> LENGTH: 16
<212> TYPE: DNA
<213> ORGANISM: Artificial Sequence
<220> FEATURE:
<223> OTHER INFORMATION: CpG D oligonucleotide

<400> SEQUENCE: 51
gggggaagct tcgggg                                                 16

<210> SEQ ID NO 52
<211> LENGTH: 13
<212> TYPE: DNA
<213> ORGANISM: Artificial Sequence
<220> FEATURE:
<223> OTHER INFORMATION: CpG K oligonucleotide

```
<400> SEQUENCE: 52
ctcgagcgtt ctc                                                        13

<210> SEQ ID NO 53
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 53
actctcgagc gttcta                                                     16

<210> SEQ ID NO 54
<211> LENGTH: 14
<212> TYPE: DNA
<213> ORGANISM: Artificial Sequence
<220> FEATURE:
<223> OTHER INFORMATION: CpG K oligonucleotide

<400> SEQUENCE: 54
tctcgagcgt tctc                                                       14

<210> SEQ ID NO 55
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 55
actctggagc gttctc                                                     16

<210> SEQ ID NO 56
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 56
tgcagcgttc tc                                                         12

<210> SEQ ID NO 57
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 57
tcgaggcttc tc                                                         12

<210> SEQ ID NO 58
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 58
gtcggcgttg ac                                                         12

<210> SEQ ID NO 59
```

```
<211> LENGTH: 19
<212> TYPE: DNA
<213> ORGANISM: Artificial Sequence
<220> FEATURE:
<223> OTHER INFORMATION: CpG K oligonucleotide

<400> SEQUENCE: 59
tcgactctcg agcgttctc                                               19

<210> SEQ ID NO 60
<211> LENGTH: 20
<212> TYPE: DNA
<213> ORGANISM: Artificial Sequence
<220> FEATURE:
<223> OTHER INFORMATION: CpG K oligonucleotide

<400> SEQUENCE: 60
atcgactctc gagcgttctc                                              20

<210> SEQ ID NO 61
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 61
tcgagcgttc tc                                                      12

<210> SEQ ID NO 62
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 62
gtcggcgtcg ac                                                      12

<210> SEQ ID NO 63
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 63
ctcgagcgtt ct                                                      12

<210> SEQ ID NO 64
<211> LENGTH: 14
<212> TYPE: DNA
<213> ORGANISM: Artificial Sequence
<220> FEATURE:
<223> OTHER INFORMATION: CpG K oligonucleotide

<400> SEQUENCE: 64
actctttcgt tctc                                                    14

<210> SEQ ID NO 65
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 65
```

```
gtcgacgttg ac                                                    12

<210> SEQ ID NO 66
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 66
actctcgagc gttctc                                                16

<210> SEQ ID NO 67
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 67
actctcgagg gttctc                                                16

<210> SEQ ID NO 68
<211> LENGTH: 20
<212> TYPE: DNA
<213> ORGANISM: Artificial Sequence
<220> FEATURE:
<223> OTHER INFORMATION: CpG K oligonucleotide

<400> SEQUENCE: 68
actctcgagc gttctcaaaa                                            20

<210> SEQ ID NO 69
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 69
catctcgagc gttctc                                                16

<210> SEQ ID NO 70
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 70
gtcgtcgatg ac                                                    12

<210> SEQ ID NO 71
<211> LENGTH: 11
<212> TYPE: DNA
<213> ORGANISM: Artificial Sequence
<220> FEATURE:
<223> OTHER INFORMATION: CpG K oligonucleotide

<400> SEQUENCE: 71
tcgagcgttc t                                                     11

<210> SEQ ID NO 72
<211> LENGTH: 12
<212> TYPE: DNA
```

```
<213> ORGANISM: Artificial Sequence
<220> FEATURE:
<223> OTHER INFORMATION: CpG K oligonucleotide

<400> SEQUENCE: 72
tcgttcgttc tc                                                          12

<210> SEQ ID NO 73
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 73
tcgtttgttc tc                                                          12

<210> SEQ ID NO 74
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 74
gtcgacgctg ac                                                          12

<210> SEQ ID NO 75
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 75
tcgatgcttc tc                                                          12

<210> SEQ ID NO 76
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 76
tcgccgcttc tc                                                          12

<210> SEQ ID NO 77
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 77
gtcatcgatg ca                                                          12

<210> SEQ ID NO 78
<211> LENGTH: 14
<212> TYPE: DNA
<213> ORGANISM: Artificial Sequence
<220> FEATURE:
<223> OTHER INFORMATION: CpG K oligonucleotide

<400> SEQUENCE: 78
actctttcga tctc                                                        14
```

<210> SEQ ID NO 79
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 79
gtcagcgtcg ac                                                     12

<210> SEQ ID NO 80
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 80
tggagcgttc tc                                                     12

<210> SEQ ID NO 81
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 81
tgctgcgttc tc                                                     12

<210> SEQ ID NO 82
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 82
ttgagcgtac tc                                                     12

<210> SEQ ID NO 83
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 83
tgcttcgagc tc                                                     12

<210> SEQ ID NO 84
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 84
tgcaccgttc tc                                                     12

<210> SEQ ID NO 85
<211> LENGTH: 12
<212> TYPE: DNA
<213> ORGANISM: Artificial Sequence
<220> FEATURE:

<223> OTHER INFORMATION: CpG K oligonucleotide

<400> SEQUENCE: 85
tgcaggcttc tc                                                            12

<210> SEQ ID NO 86
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 86
ttgagtgttc tc                                                            12

<210> SEQ ID NO 87
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 87
gtcggcgctg ac                                                            12

<210> SEQ ID NO 88
<211> LENGTH: 20
<212> TYPE: DNA
<213> ORGANISM: Artificial Sequence
<220> FEATURE:
<223> OTHER INFORMATION: CpG K oligonucleotide

<400> SEQUENCE: 88
atgcactctg caggcttctc                                                    20

<210> SEQ ID NO 89
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 89
gtcagcgctg ac                                                            12

<210> SEQ ID NO 90
<211> LENGTH: 7
<212> TYPE: DNA
<213> ORGANISM: Artificial Sequence
<220> FEATURE:
<223> OTHER INFORMATION: CpG K oligonucleotide

<400> SEQUENCE: 90 tcgagcg                                                                   7

<210> SEQ ID NO 91
<211> LENGTH: 10
<212> TYPE: DNA
<213> ORGANISM: Artificial Sequence
<220> FEATURE:
<223> OTHER INFORMATION: CpG K oligonucleotide

<400> SEQUENCE: 91
tcgagcgttc                                                               10

```
<210> SEQ ID NO 92
<211> LENGTH: 9
<212> TYPE: DNA
<213> ORGANISM: Artificial Sequence
<220> FEATURE:
<223> OTHER INFORMATION: CpG K oligonucleotide

<400> SEQUENCE: 92 tcgagcgtt                                                                 9

<210> SEQ ID NO 93
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 93
gtcaacgctg ac                                                            12

<210> SEQ ID NO 94
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 94
gtcaacgtcg ac                                                            12

<210> SEQ ID NO 95
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 95
gtcgacgccg ac                                                            12

<210> SEQ ID NO 96
<211> LENGTH: 8
<212> TYPE: DNA
<213> ORGANISM: Artificial Sequence
<220> FEATURE:
<223> OTHER INFORMATION: CpG K oligonucleotide

<400> SEQUENCE: 96 tcgagcgt                                                                  8

<210> SEQ ID NO 97
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 97
gggggaacgt tggggg                                                        16

<210> SEQ ID NO 98
<211> LENGTH: 12
<212> TYPE: DNA
<213> ORGANISM: Artificial Sequence
<220> FEATURE:
<223> OTHER INFORMATION: CpG K oligonucleotide
```

-continued

<400> SEQUENCE: 98
tgcagcgagc tc                                                           12

<210> SEQ ID NO 99
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 99
ccgaggcttc tc                                                           12

<210> SEQ ID NO 100
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 100
acgagggttc tc                                                           12

<210> SEQ ID NO 101
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 101
gtcaacgccg ac                                                           12

<210> SEQ ID NO 102
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 102
gcgaggcttc tc                                                           12

<210> SEQ ID NO 103
<211> LENGTH: 16
<212> TYPE: DNA
<213> ORGANISM: Artificial Sequence
<220> FEATURE:
<223> OTHER INFORMATION: CpG K oligonucleotide

<400> SEQUENCE: 103
actcttgagt gttctc                                                       16

<210> SEQ ID NO 104
<211> LENGTH: 12
<212> TYPE: DNA
<213> ORGANISM: Artificial Sequence
<220> FEATURE:
<223> OTHER INFORMATION: CpG K oligonucleotide

<400> SEQUENCE: 104
gtcggcgccg ac                                                           12

<210> SEQ ID NO 105
<211> LENGTH: 12

```
-continued
<212> TYPE: DNA
<213> ORGANISM: Artificial Sequence
<220> FEATURE:
<223> OTHER INFORMATION: CpG K oligonucleotide

<400> SEQUENCE: 105
gtcagcgccg ac                                                              12

<210> SEQ ID NO 106
<211> LENGTH: 11
<212> TYPE: DNA
<213> ORGANISM: Artificial Sequence
<220> FEATURE:
<223> OTHER INFORMATION: CpG K oligonucleotide

<400> SEQUENCE: 106
cgagcgttct c                                                               11
```